United States Patent
Goris et al.

(10) Patent No.: US 11,416,999 B2
(45) Date of Patent: Aug. 16, 2022

(54) METHODS, SYSTEMS, AND COMPUTER PROGRAMS FOR SEGMENTING A TOOTH'S PULP REGION FROM AN IMAGE

(71) Applicant: Medicim NV, Mechelen (BE)

(72) Inventors: Bart Goris, Emblem (BE); Pieter Van Leemput, Rumst (BE); Wouter Mollemans, Antwerp (BE); An Elen, Rijmenam (BE)

(73) Assignee: Medicim NV, Mechelen (BE)

( * ) Notice: Subject to any disclaimer, the term of this patent is extended or adjusted under 35 U.S.C. 154(b) by 68 days.

(21) Appl. No.: 17/058,094

(22) PCT Filed: May 28, 2019

(86) PCT No.: PCT/EP2019/063883
§ 371 (c)(1),
(2) Date: Nov. 23, 2020

(87) PCT Pub. No.: WO2019/229092
PCT Pub. Date: Dec. 5, 2019

(65) Prior Publication Data
US 2021/0209764 A1 Jul. 8, 2021

(30) Foreign Application Priority Data

May 29, 2018 (EP) .................................... 18174919

(51) Int. Cl.
*G06T 7/11* (2017.01)
*G06T 7/136* (2017.01)
(Continued)

(52) U.S. Cl.
CPC .................. *G06T 7/11* (2017.01); *A61B 6/14* (2013.01); *G06T 7/0014* (2013.01); *G06T 7/136* (2017.01);
(Continued)

(58) Field of Classification Search
USPC ........................................ 382/128, 132, 173
See application file for complete search history.

(56) References Cited

U.S. PATENT DOCUMENTS

| 11,166,688 | B2* | 11/2021 | Mandelkern | ............. A61B 6/14 |
| 2002/0037489 | A1* | 3/2002 | Jones | ................... A61C 9/0046 |
| | | | | 433/213 |

(Continued)

FOREIGN PATENT DOCUMENTS

CN 106 570 859 A 4/2017

OTHER PUBLICATIONS

C. Lost, Quality guidelines for endodontic treatment: consensus report of the European Society of Endodontology, *International Endodontic Journal*, 39:921-930, dated 2006.
(Continued)

*Primary Examiner* — Ishrat I Sherali
(74) *Attorney, Agent, or Firm* — Knobbe, Martens, Olson & Bear, LLP

(57) ABSTRACT

Methods, systems, and computer programs are disclosed for segmenting, from an image, a tooth's pulp region comprising a pulp chamber and root canals. Curvature-based shape recognition is performed at different spatial scales using smoothed versions of the image. An indication of a point or region is received, located in the pulp chamber and referred to as "seed". The seed is used as initial segmentation mask. An update procedure, iteratively carried out, comprises: (i) determining candidate image elements for updating the segmentation mask, comprising: (i-1) in the first n iteration(s), a grayscale thresholding taking as reference the current segmentation mask; and, (i-2) in at least one iteration, taking the curvature-based shape recognition into account; (ii) retaining, among the candidate image elements, a region of connected candidate image elements that com- (Continued)

prises the seed; and (iii) using the retained region to update the segmentation mask.

26 Claims, 12 Drawing Sheets

(51) Int. Cl.
    *G06T 7/194* (2017.01)
    *G06T 7/50* (2017.01)
    *A61B 6/14* (2006.01)
    *G06T 7/00* (2017.01)
    *G06V 10/25* (2022.01)
    *G06V 10/44* (2022.01)

(52) U.S. Cl.
    CPC ............... *G06T 7/194* (2017.01); *G06T 7/50* (2017.01); *G06V 10/25* (2022.01); *G06V 10/44* (2022.01); *G06T 2207/10116* (2013.01); *G06T 2207/30036* (2013.01); *G06V 2201/03* (2022.01)

(56) References Cited

U.S. PATENT DOCUMENTS

2014/0314291 A1* 10/2014 Souza ................... G06T 7/0012 382/131
2020/0146773 A1* 5/2020 Levin ................. G05B 19/4099
2020/0320685 A1* 10/2020 Anssari Moin ........ G06V 10/26

OTHER PUBLICATIONS

Dentsply Sirona, 3D Endo™ Software brochure, https://www.3dendo.com/, dated Mar. 2018.

A.F. Frangi, W.J. Niessen, L. Vincken, and M.A. Viergever, Multiscale vessel enhancement filtering, *Lecture Notes in Computer Science*, 1496:130-137, dated 1998.
M. Descoteaux, M. Audette, K. Chinzel, and K. Siddiqi, Bone enhancement filtering: Application to sinus bone segmentation and simulation of pituitary surgery, *Computer aided surgery*, 11(5):247-255, dated 2010.
S. Lankton and A. Tannenbaum, Localizing region-based active contours, *IEEE Transactions on Image Processing*, 17(11):2029-2039, dated 2008.
F. Peracchi, Robust m-estimators of regression, *Giornale degli Economisli e Annali di Economia*, 46(9):533-545, dated 1987.
C. Jud and T. Vetter, Using object probabilities in deformable model fitting, *2014 22nd International Conference on Pattern Recognition*, 3310-3314, dated 2014.
Jud Christopher et al.: "Using Object Probabilities in Deformable Model Fitting", International Conference on Pattern Recognition, IEEE Computer Society, US, dated Aug. 24, 2014, pp. 3310-3314.
Gyehyun Kim et al.; "Automatic Teeth Axes Calculation for Well-Aligned Teeth Using Cost Profile Analysis Along Teeth Center Arch", IEEE Transactions on Biomedical Engineering, IEEE Service Center, Piscataway, NJ, USA, vol. 59, No. 4, dated Apr. 1, 2012, pp. 1145-1154.
Jérôme Michetti et al: "Comparison of an adaptive local thresholding method on CBCT and CT endodontic images", Physics in Medicine and Biology, Institute of Physics Publishing, Bristol GB, vol. 63, No. 1, dated Dec. 18, 2017, p. 15020.
Balázs Benyó: "Identification of dental root canals and their medial line from micro-CT and conebeam CT records", Biomedical Engineering Online, Biomed Central Ltd, London, GB, vol. 11, No. 1, dated Oct. 29, 2012, p. 81.
International Search Report for International Application No. POT/EP2019/063883 by European Patent Office dated Jul. 16, 2019.

* cited by examiner

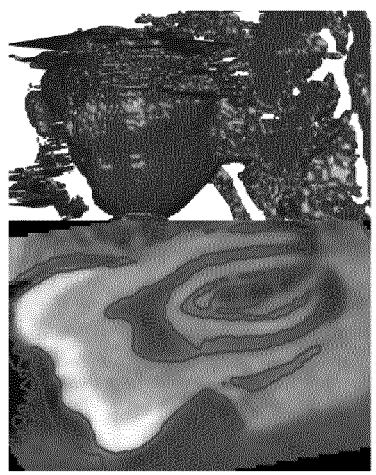
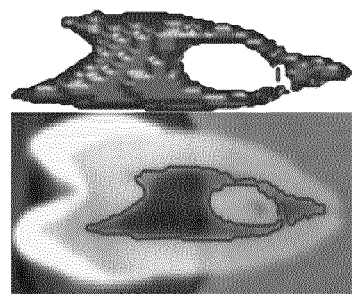
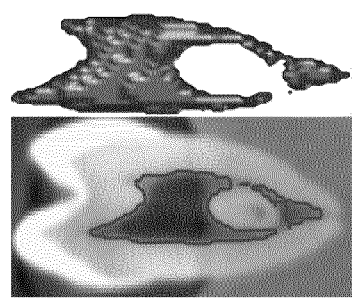
(a) Tooth 1.5 (b) Tooth 1.2
Fig. 12
(a) Extracted tooth 2.1, $f_s = 1$ (b) Extracted tooth 2.2, $f_s = 1$ (c) Extracted tooth 2.2, $f_s = 2$
Fig. 13

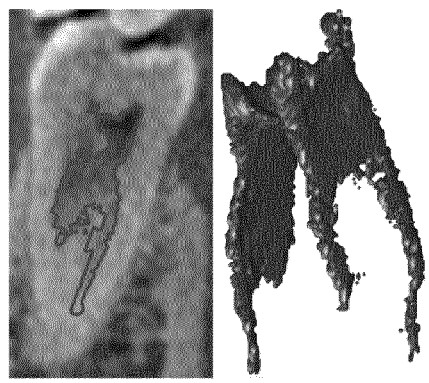 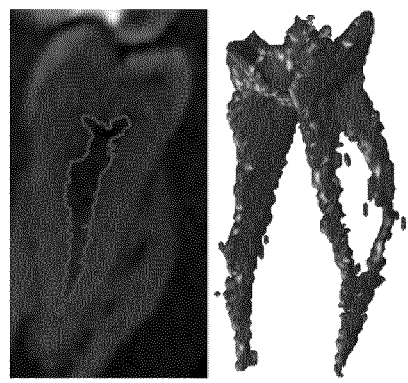
(a) CBCT tooth 3.1    (b) CBCT tooth 3.2
Fig. 14
(a)    (b)
Fig. 15

__US 11,416,999 B2__

METHODS, SYSTEMS, AND COMPUTER PROGRAMS FOR SEGMENTING A TOOTH'S PULP REGION FROM AN IMAGE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is filed under 35 U.S.C. § 371 as the U.S. National Phase of Application No. PCT/EP2019/063883 entitled "METHODS, SYSTEMS, AND COMPUTER PROGRAMS FOR SEGMENTING A TOOTH'S PULP REGION FROM AN IMAGE" and filed May 28, 2019, and which claims priority to EP 18174919.3 filed May 29, 2018, each of which is incorporated by reference in its entirety.

BACKGROUND OF THE INVENTION

Field of the Invention

The present development relates to methods for segmenting a tooth's pulp region from a two-dimensional (2D) or three-dimensional (3D) image of said tooth. The development also relates to systems for carrying out such methods, and to computer programs therefor. Some embodiments of the development may for example be used for planning an endodontic treatment.

Description of the Related Art

Teeth have a soft interior core containing nerves and relatively small blood vessels. This core is called the pulp region or dental pulp region and extends from the crown of the tooth to the tip of the tooth's root in the jawbone. When a tooth is cracked or has a deep cavity, bacteria may enter the pulp and cause serious infections. When untreated, such infections of the root canal may result in pulp death, jaw bone loss and loss of the tooth itself (see ref. [1]; a list of references being provided at the end of the present description). These infections can be treated by cleaning the root canal and filling it with an inert material such as gutta-percha. Treatments of the root canals are usually performed by an endodontist or a general dentist. Typically, a dental X-ray scan is first acquired to inspect the extent of the damage and the infection. Next, an opening is made in the crown of the tooth to gain access to the pulp chamber. Then, small files and an aqueous solution are used to clean the root canals, remove the dental nerves and possibly also the infected pulp. At the end of the treatment, the cleaned canal is filled with gutta-percha and the entrance hole in the crown is closed again (ref. [1]).

A difficulty during root canal treatment is cleaning and filling all root canals over their entire length. If parts are missed, infections are likely to occur afterwards. In addition, the endodontist should not clean beyond the length of a canal to avoid damaging the mandibular nerve to which the root nerve is attached. This may potentially cause serious pain and inflammations for the patients. Some teeth have complex canal shapes that are hard to visualize using a 2D or even a 3D image. Such a 3D visualization may be obtained using 3D cone beam computed tomography (CBCT) data.

In an existing endodontic planning tool for the 3D investigation of root canals (ref. [2]), the user first has to determine the number of root canals that are present in each tooth. For each of the root canals, the position of the start and end points must be indicated on a 2D slice visualization of the 3D volume. In addition, the entire 3D pathway of the root canal needs to be outlined manually by clicking a set of control points. Based on this manual input, a 3D visualization of the shape of the central line of the root canals can be obtained.

Jud et al. (ref. [7]) disclose a method for segmenting a tooth shape from a 3D CBCT dataset of the jaw region. In a first step the method comprises predicting for the image elements the probability that they belong to a tooth object. Thereafter, a statistical tooth shape model is fitted to these object probabilities, thus providing a segmentation of the shape. Although the method of Jud et al. allows predicting the probability that an image element is within the pulp region, the authors indicate that the high variability in between teeth of the shape of the pulp region is incongruent with building a statistical pulp shape model and registering such model to pulp object probabilities. As such the method of Jud et al. cannot be used for segmenting the pulp region of a tooth.

It is desirable to improve the prior art methods notably by making them less time-consuming for users, more effective in visualizing special characteristics of root canals, and more suitable for planning an endodontic treatment.

SUMMARY

To meet or at least partially meet the above-mentioned goals, methods, systems, and computer programs according to the development are defined in the independent claims. Particular embodiments are defined in the dependent claims.

In one embodiment, a method is implemented, i.e. carried out, by a computer, or by a set of computers, for segmenting a tooth's pulp region from a 2D or 3D image of said tooth. Said pulp region comprises a pulp chamber and one or more root canals. The method comprises the following operations. Curvature-based shape recognition is performed at different spatial scales using smoothed versions of the image. An indication of a point or region is received, which is assumed to be located in the imaged pulp chamber of the image and corresponds to at least one image element of the image, the at least one image element being hereinafter referred to as "seed". At least the seed is then used as initial segmentation mask. A procedure, hereinafter referred to as "update procedure", is then iteratively carried out. The update procedure comprises: (i) determining candidate image elements for updating the segmentation mask, wherein determining comprises: (i-1) in at least the first n iteration(s) of the update procedure, a grayscale thresholding taking as reference the current segmentation mask, wherein n is a nonzero positive integer; and, (i-2) in at least one iteration of the update procedure, taking the curvature-based shape recognition into account; (ii) retaining, among the candidate image elements, a region of connected candidate image elements that comprises the seed; and (iii) using the retained region to update the segmentation mask.

This enables the efficient and automatic segmentation of a pulp region from 2D or 3D image data starting from a (e.g., user-selected) seed point in the pulp chamber. In particular, an iterative process enables the segmentation of the pulp region. In the iterative process, the grayscale thresholding (GT) aims at detecting the pulp region based on intensity values of image elements, whereas the curvature-based shape recognition (CBSR) applied to the image elements complements and combines with the GT to detect typical structures of root canals, such as tubular and sheet-like shapes, while discarding parts unlikely to constitute root canals. Further, the method is well suited to enable, in at least some embodiments, the detection of potentially intricate shapes of certain root canals, including bifurcations and obstructions therein, so as to eventually enable the convenient and precise planning of an endodontic treatment.

The development further relates, in one embodiment, to a system for segmenting a tooth's pulp region from a 2D or 3D image of said tooth, wherein said pulp region comprises, as mentioned above, a pulp chamber and one or more root canals. The system comprises a processing unit configured for carrying out the operations of the above-described method.

The development also relates to computer programs, computer program products and storage mediums comprising computer-readable instructions configured, when executed on a computer, to cause the computer to carry out the above-described method, or to implement the functions of a system as described above.

BRIEF DESCRIPTION OF THE DRAWINGS

Embodiments of the present development shall now be described, in conjunction with the appended figures, in which:

FIG. 4 shows, to assist in understanding the context of some embodiments of the development, examples of root canal shapes, wherein FIGS. 4a to 4c show 3D visualization of possible root canals including difficulties such as bifurcations (FIG. 4b) and open apices (FIG. 4c), and FIGS. 4d to 4f show 2D slices through corresponding 3D CBCT volumes;

FIG. 12 shows, to assist in understanding some embodiments of the development, results of root canal segmentation for two teeth of data set No. 1, after extra iterations with featureness sensitivity factor $f_s=2$, where, in FIG. 12(a), a small bifurcation near the apex of tooth 1.5 is captured, while, in FIG. 12(b), for tooth 1.2, the segmentation diverges outside of the root canal, using the higher $f_s$ value;

FIG. 13 shows, to assist in understanding some embodiments of the development, results of root canal segmentation for two teeth of data set No. 2 with extracted teeth;

FIG. 14 shows, to assist in understanding some embodiments of the development, results of root canal segmentation for two teeth of data set No. 3 with (not special-purpose endo) CBCT images;

FIG. 15 schematically illustrates, to assist in understanding some embodiments of the development, a distance map pruning on toy data, wherein, for illustrative reasons, Manhattan distance and parameter c=3 are used, wherein values larger than $[d_{max}-c]$ are pruned to $[d_{max}-c]$, with $d_{max}$ being a local maximum value. FIG. 15(a) shows the initial distance map (distance to start voxel (square)) with two local maxima (stars); and FIG. 15(b) shows pruned distance values (underlined values) with indication of the local maximum region (circles), wherein, within this region, the local maximum of the initial distance function is selected as the final apex candidate (star).

FIG. 16 schematically illustrates, to assist in understanding some embodiments of the development, the definition of the apex voxels on real data, wherein FIG. 16(a) shows local maxima (stars) of the distance map Dg to the start voxel $p_{start}$ (white square), and FIG. 16(b) shows local maxima regions (circles) of the pruned distance function and local maxima of the original distance function Dg in these regions (stars and white triangle)

DETAILED DESCRIPTION OF CERTAIN EMBODIMENTS

The present development shall now be described in conjunction with specific embodiments. These specific embodiments serve to provide the skilled person with a better understanding, but are not intended to in any way restrict the scope of the development, which is defined by the appended claims. A list of abbreviations and their meaning is provided at the end of the detailed description.

Figure 1:
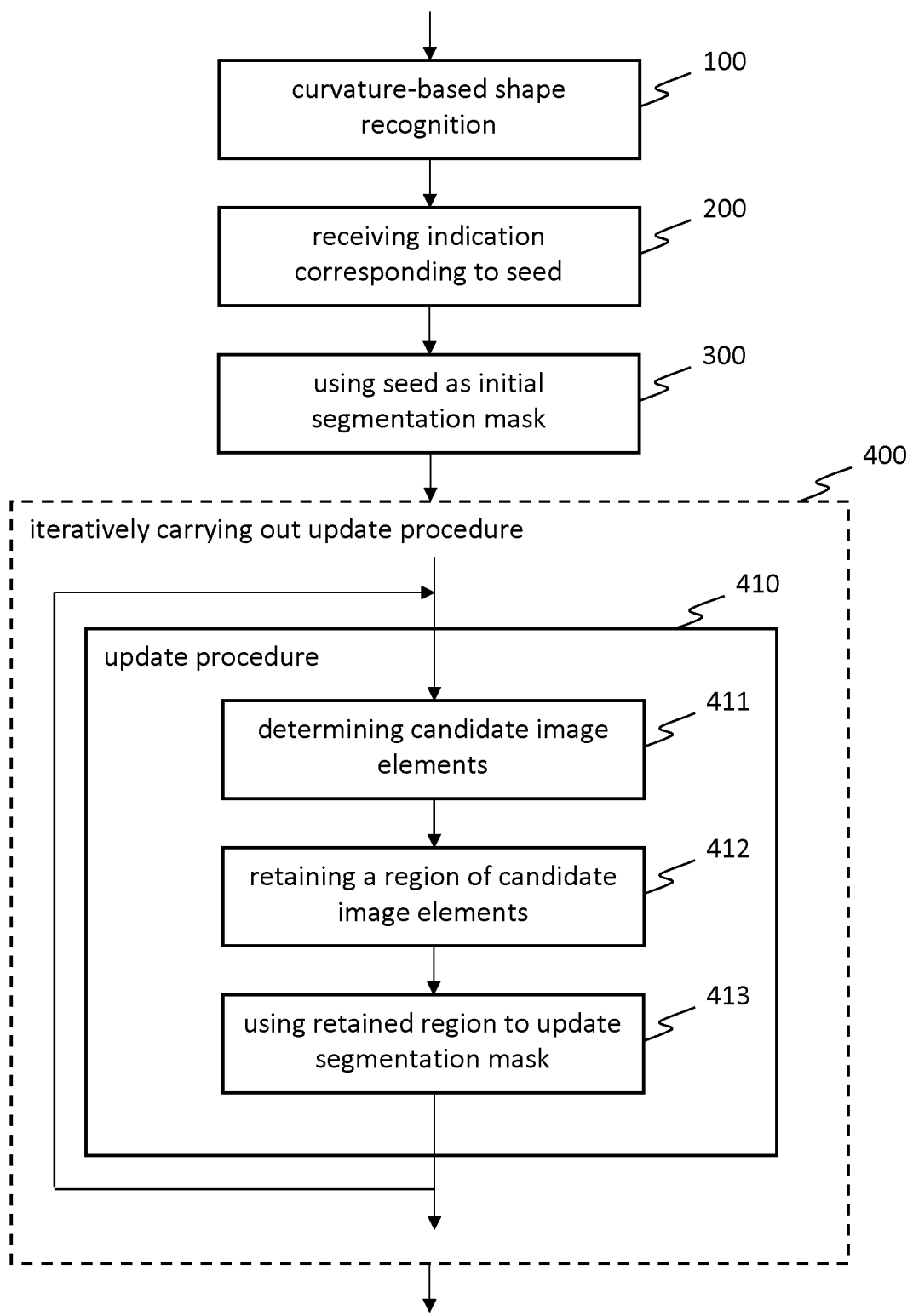
FIG. 1 is a flowchart of a method in one embodiment of the development.

FIG. 1 is a flowchart of a method in one embodiment of the development. The method is computer-implemented. That is, the method may be carried out by a computer or set of computers, although the development is not limited thereto. The method may also be implemented, as a form of computer-implemented method, using hardware electronic circuits, e.g. with field-programmable gate arrays (FPGA), or using a combination of computer(s) and hardware electronic circuits.

The method aims at segmenting a tooth's pulp region from a 2D or 3D image of said tooth. The pulp region comprises a pulp chamber and one or more root canals, also called "radicular canals". The pulp region, or dental pulp region, comprises the dental pulp. By "segmenting", it is here referred to the technique of image segmentation in which one or more segment within a digital image is identified, extracted, or, in other words, delineated. In the present method, the segment(s) to be identified is the tooth's pulp region comprising the pulp chamber and one or more root canals.

The input image may be a 2D or 3D image. In one embodiment, the image is an X-ray image, such as for example a 3D image produced by cone beam computed tomography (CBCT). In one embodiment, the image is a slice or a 2D projection image of a 3D image. The computer(s) and/or electronic circuit(s) carrying out the method may be part of an imaging apparatus configured to acquire the image data, or may be separated therefrom. The image data may be inputted to the computer(s) and/or electronic circuit(s) by any means, such as for example through a wired or wireless transfer, or by manually removing a storage medium (e.g., a removable memory card or an optical disk) from an imaging apparatus and plugging it into the computer(s) and/or electronic circuit(s) configured to carry out the method. Furthermore, the image data may be stored in accordance with any type of format and/or standard, such as for example the DICOM standard.

The method illustrated in FIG. 1 comprises the following steps. In FIG. 1, the arrow reaching the top box of the flowchart represents the start of the method. However, additional steps may be performed prior to the steps depicted in FIG. 1, such as for example steps pertaining to the acquisition and/or pre-processing of the input image (see also section 2.A below).

In step 100, a curvature-based shape recognition (CBSR) process is performed at different spatial scales (i.e., in accordance with a multiscale approach, as further explained below in section 2.C) using smoothed versions of the image (as further explained in section 2.C). A CBSR process is a procedure for recognition of a shape encompassing an image element by determining the directions of curvature at the level of said image element, considering that a shape is completely defined by these curvature directions.

In one embodiment, the CBSR procedure comprises a multiscale approach wherein for each image element the principal directions of curvature are determined at different degrees of image smoothening.

In some embodiments, the CBSR process applied to the image specifically aims at detecting typical structures of root canals, such as tubular and sheet-like shapes, while discarding parts unlikely to constitute root canals. A form of CBSR term computation is further explained in section 2.C below. Further, the detection of respectively tubular and plate-like shapes using CBSR is known from ref. [3] and ref. [4] for, respectively, the detection of blood vessels and paranasal sinus bones in medical images.

In step 200, an indication of a point or region of the image is received. The point or region is assumed to be located in the imaged pulp chamber of the image, i.e. in the part of the image corresponding to the pulp chamber. This means that, prior to step 200, a user may be shown the image (for example on a computer display, or a volumetric display device), and the user may be asked to select a point or region thereof, which the user considers to be located in the pulp chamber. The coordinates of the selected point or region are then received by, such as obtained by or inputted to, the computer(s) and/or electronic circuit(s) configured to carry out the method. The user may select the point or region using any technical means, such as a pointing device (e.g., a computer mouse, a touchpad, a trackball, a joystick, or a pointing stick) controlling a pointer on a display, or a finger or stylus pen to indicate a point on a touchscreen-based graphical user interface (GUI). In one embodiment, the user is asked to select a point or region located centrally within the pulp region, i.e. relatively far from the edge of the pulp region.

The selected point or region corresponds to one or more image element of the image, said image element(s) being hereinafter referred to as "seed". In one embodiment, an image element is a voxel. In another embodiment, an image element is a pixel. The seed may be the single voxel or pixel corresponding to a point selected by the user. Alternatively, the seed may be a plurality of voxels or pixels corresponding to a region of points selected by the user. The seed may also comprise the voxel(s) or pixel(s) corresponding to a point selected by the user and a number of neighbouring voxels or pixels (see also section 2.B below).

In one embodiment, a point or region of the image is automatically selected (e.g., by a computer or a computer program), rather than by a user. For instance, from a starting point on the occlusal surface of a tooth, a computer program can automatically analyze the pixel/voxel intensity in an apical direction of the tooth resulting in respectively detection of high intensity pixels/voxels of the enamel, medium intensity pixels/voxels of the dentine, and low intensity pixels/voxels of the pulp chamber, and subsequently select a low intensity voxel/pixel of the pulp chamber as seed. In one embodiment, the user selection of a point or region of the image is a computer-assisted or computer-aided selection. 90

In step 300, a segmentation mask is then initialised as comprising at least the seed, i.e. the seed and, optionally, additional image elements selected for example through a pre-processing operation. The segmentation mask is the initial segmentation mask that will be used and then updated in step 400. A segmentation mask is a set of image elements from the original image.

In step 400, a procedure 410, here referred to as "update procedure", is iteratively carried out, starting from the (e.g., user-indicated) seed point located in the pulp chamber, i.e. starting based on the initial segmentation mask from step 300. The goal of update procedure 410 is to update the segmentation mask, and the goal of the iteration process 400 is to eventually output the pulp region segmentation. Update procedure 410 comprises sub-steps 411, 412, and 413, which may be described as follows:

In sub-step 411, candidate image elements are determined for updating the segmentation mask. The sub-step of determining 411 comprises:

(i-1) in at least the first n iteration(s) of update procedure 410, a grayscale thresholding (GT) taking as reference the current segmentation mask, wherein n is a nonzero positive integer; and, (i-2) in at least one iteration of update procedure 410, taking the curvature-based shape recognition (CBSR) (computed in step 100) into account.

The grayscale thresholding (GT), which may be a local gray level estimation, aims at overcoming partial volume effects (PVE) during segmentation. A grayscale thresholding (GT) process is a transformation of grayscale image data into, preferably binary, image data based on a threshold or on a plurality of thresholds (e.g., the threshold value may locally be adapted depending on local image characteristics). Typically, the GT taking as reference the current segmentation mask as used in the present development comprises determining the differences between the intensity level of an image element under consideration and an averaged foreground and background intensity value, respectively. The averaged foreground value is computed as the average intensity value of image elements comprised in the current segmentation mask and the averaged background intensity value is computed as the average intensity value of image elements outside the current segmentation mask. Preferably, the averaged background and foreground intensity values are local values reflecting average intensity values within the neighborhood of the image element under investigation. For instance, said local averaged foreground and background intensity values may be computed for the image elements within an image region centered around said image element under consideration. Alternatively, said local averaged foreground and/or background intensity values may be calculated as weighted averages, wherein the weight of the intensity value of an image element decreases with increasing distance between said image element and the image element under consideration. Such weighted average intensity background and foreground values can be calculated using a weighing mask, which is preferably centered around said image element under consideration. Such weighing mask may be a Gaussian stencil centered around the image element under consideration, for instance a Gaussian stencil with a standard deviation of 0.8 mm. The GT process is further discussed in section 2.D below.

During each of the iterations, determining sub-step 411 depends on the GT, on the CBSR, or on a combination of GT and CBSR.

Table 1 provides examples of compositions of determining sub-step 411, for values of n equal to 1, 2, 3, 4, and 5, in an embodiment in which five iterations of an update procedure 410 are carried out.

TABLE 1

|  | n | iteration 1 | iteration 2 | iteration 3 | iteration 4 | iteration 5 |
|---|---|---|---|---|---|---|
| Example 1 | 1 | GT | CBSR | CBSR | CBSR | CBSR |
| Example 2 | 1 | GT, CBSR | CBSR | CBSR | CBSR | CBSR |
| Example 3 | 2 | GT | GT | CBSR | CBSR | CBSR |
| Example 4 | 2 | GT | GT, CBSR | CBSR | CBSR | CBSR |
| Example 5 | 2 | GT, CBSR | GT, CBSR | CBSR | CBSR | CBSR |
| Example 6 | 3 | GT | GT | GT | CBSR | CBSR |
| Example 7 | 3 | GT | GT | GT, CBSR | CBSR | CBSR |
| Example 8 | 3 | GT, CBSR | GT, CBSR | GT, CBSR | CBSR | CBSR |
| Example 9 | 4 | GT | GT | GT | GT | CBSR |
| Example 10 | 4 | GT | GT | GT, CBSR | GT, CBSR | CBSR |
| Example 11 | 4 | GT, CBSR | GT, CBSR | GT, CBSR | GT, CBSR | CBSR |
| Example 12 | 5 | GT | GT | GT | GT | GT, CBSR |
| Example 13 | 5 | GT | GT | GT | GT, CBSR | GT, CBSR |
| Example 14 | 5 | GT | GT | GT, CBSR | GT, CBSR | GT, CBSR |
| Example 15 | 5 | GT | GT, CBSR | GT, CBSR | GT, CBSR | GT, CBSR |
| Example 16 | 5 | GT | GT, CBSR | GT, CBSR | GT, CBSR | GT |
| Example 17 | 5 | GT, CBSR | GT, CBSR | GT, CBSR | GT, CBSR | GT, CBSR |

In example 1, during the first iteration of update procedure 410, determining sub-step 411 depends on the GT, whereas the CBSR is switched off. Then, during the four subsequent iterations, sub-step 411 depends on the CBSR, whereas the GT is switched off.

In example 2, during the first iteration, both the GT and CBSR are switched on in sub-step 411. Then, during the four subsequent iterations, the CBSR is switched on, whereas the GT is switched off.

In example 3, during the first two iterations, the GT is switched on, whereas the CBSR is switched off. Then, during the three subsequent iterations, the CBSR is switched on, whereas the GT is switched off.

A skilled person will understand examples 4 to 17 of Table 1 in a similar manner.

In other embodiments, the number of iterations of the update procedure 410 is different from 5, such as 2, 3, 4, 6, 7, 8, 9, or 10. The total number of iterations may be a predetermined number or may depend on runtime conditions. In one embodiment, the total number of iterations depends on the extent to which the size of the segmentation mask is changing from one iteration to the next. For example, if the size of the segmentation mask is not changing by more than a threshold number of image elements, the iterative process 400 may be terminated. In other words, the iteration process 400 may continue until the difference between the number of image elements in the segmentation masks obtained in two successive iterations is smaller than a threshold value (e.g., a value comprised between 5 and 20).

The number n of iterations during which the GT is carried out as part of the sub-step 411 of determining candidate image elements may as well be a predetermined number or may depend on runtime conditions. In one embodiment, the GT is performed in all iterations of update procedure 410.

During each iteration, sub-step 411 outputs one or a plurality of regions of connected candidate image elements.

In sub-step 412, the region of connected candidate image elements that comprises the seed is selected and retained among the candidate image elements. A first candidate image element and a second candidate image element are connected if there is a path of candidate image elements from the first candidate image element to the second candidate image element.

Then, in sub-step 413, the retained region is used to update the segmentation mask. That updated segmentation mask is then used as current segmentation mask for the next iteration, if any, of the update procedure 410.

In the method, step 100 need not necessarily be performed prior to step 200. Step 100 may alternatively be performed after step 200 or in parallel thereto, after step 300 or in parallel thereto, or even at a point in time when the iterative process 400 is already under way.

The method therefore enables the avoidance, as much as possible, of user intervention in detecting the shape of a tooth's pulp region, including its root canals. That is, the method enables the process to be as automated as possible. In particular, to segment both the shape and the centerline of the root canals, it is not necessary for the user to indicate the start and endpoint of the canals. Only a single point in the pulp chamber may be selected, making the method user-friendlier and more reliable than the method of ref. [2]. Generally, all root canals can be found in a tooth starting from a (e.g., user-indicated) seed point in the pulp chamber. In addition, the method generally enables to compensate for partial volume effects (PVE) which may happen due to the limited resolution of the 3D data. This effect occurs when multiple tissue types are present in the same voxel of the 3D volume yielding gray values which are a mixture of the gray values of the individual tissues. This effect is particularly significant at the narrow tip point of the root canal. The 3D segmentation volume resulting from the method generally clearly shows the shape of the root canals, as well as their bifurcating (i.e., splitting and/or merging) behaviour.

The method also enables the handling of some special cases. First, the case of an open apex can generally be well handled. This case occurs mostly with children in the age of 7 to 14 years for whom the tooth is not yet fully grown yielding a root canal which is open at the apex of the tooth. Second, the case of an apical delta can also generally be well handled. Such an apical delta implies that the root canal splits in different small channels with a diameter of approximately 100 μm (micrometer) close to the apical foramen.

In one embodiment, in at least one iteration of the update procedure 410, the grayscale thresholding (GT) and the curvature-based shape recognition (CBSR) are both performed. Examples 2, 4, 5, 7, 8, and 10 to 17 shown in Table 1 are examples of such an embodiment. In such a case, the CBSR complements and combines with the GT to enable the detection of typical structures of root canals, such as tubular and sheet-like shapes, while discarding parts unlikely to constitute root canals.

In one embodiment, in at least one iteration in which GT and CBSR are both performed, an importance or weight associated, for an image element under consideration, to the CBSR relative to the GT increases with increasing distance of the image element from the seed. In other words, in at least one iteration, determining 411 whether an image element qualifies as a candidate image element for updating the segmentation mask depends on both GT and CBSR, and the farther away the image element is from the seed, the greater the relative importance of the CBSR is in the determination 411. This feature accounts for the fact that, when an image element is relatively far away from the seed, the image element more likely belongs to a root canal than to the pulp chamber. In other words, with increasing distance from the seed point, the filter underlying determination step 411 is more and more tuned to better exploit the inherent shape of the canal by increasing the weight of the CBSR component in the filter. An image filter is a technique through which size, intensity, color, shading and/or other characteristics of an image are altered, for instance enhanced.

In one embodiment, in at least one iteration during which the CBSR is performed, determining candidate image elements further takes into account a directionality of a recognized shape at the level of an image element in comparison to an overall directionality of a portion of the segmentation mask near said image element. This process is further explained in section 3.E below.

This embodiment has the advantage of taking the inherent directionality of a root canal into account. In particular, taking the directionality of a recognized shape into account allows, first, for a better identification of narrow end sections of a root canal. Second, it allows for a more robust segmentation if noise is present in the original image data close to the pulp region. Third, it also provides for an adequate termination of the segmentation in case of open-ended root canals (as previously discussed). Such open-ended root canals are common in children but rare in adults.

Figure 2:
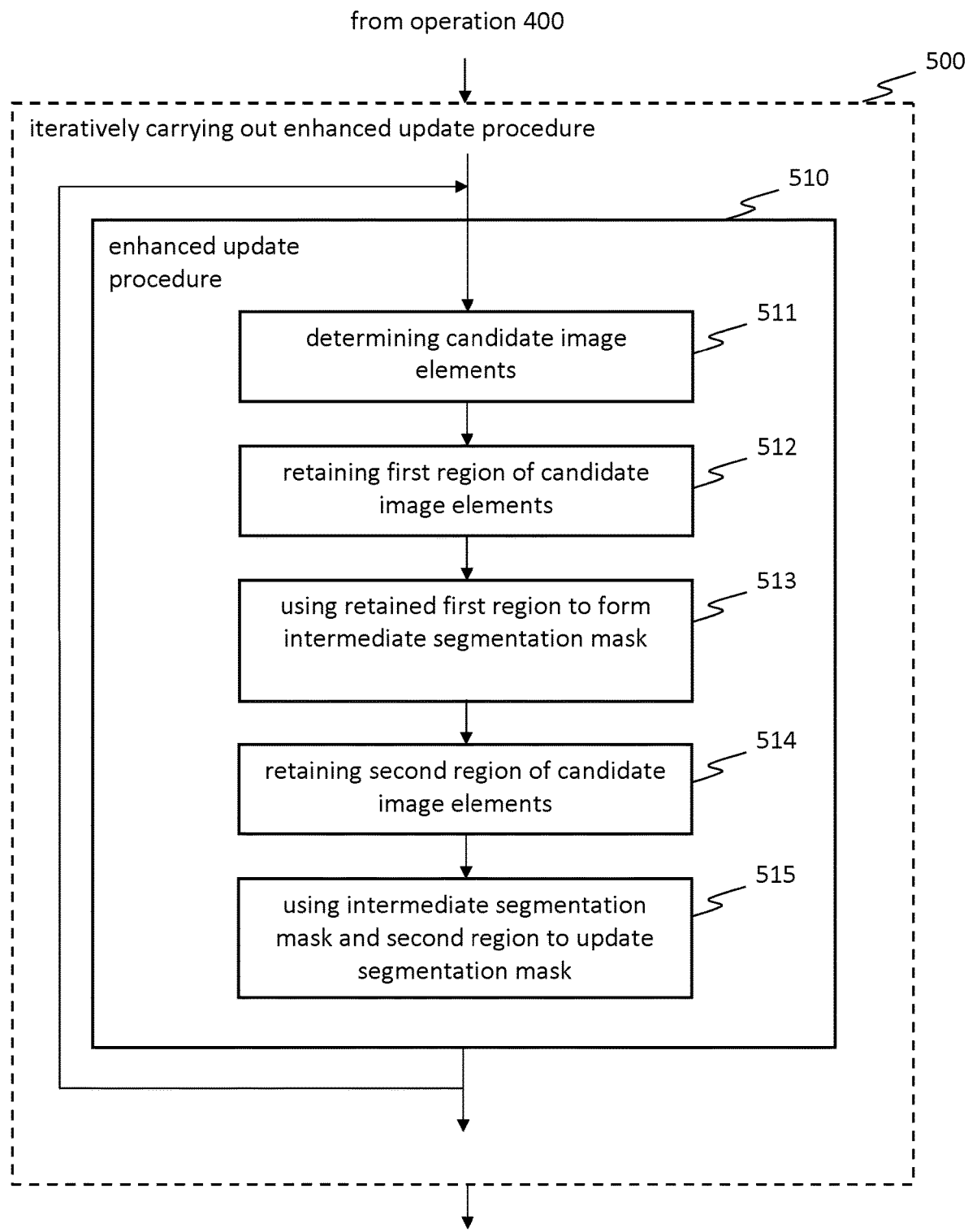
FIG. 2 is a flowchart of a method in one embodiment of the development, further comprising, compared to the flowchart of FIG. 1, iteratively carrying out an enhanced update procedure.

FIG. 2 is a flowchart of a method in one embodiment of the development, comprising iteratively carrying out 500 a further procedure 510, here referred to as "enhanced update procedure". Iteratively carrying out 500 the enhanced update procedure 510 is performed after having iteratively carried out 400 the update procedure 410, as illustrated by the mention "from operation 400" on the top of FIG. 2.

Enhanced update procedure 510 comprises the following sub-steps:

In sub-step 511, candidate image elements for updating the segmentation mask are determined. The segmentation mask that is initially used in the first iteration of enhanced update procedure 510 is the segmentation mask outputted by the last iteration of update procedure 410. Sub-step 511 comprises taking into account the CBSR and a directionality of a recognized shape at the level of an image element in comparison to an overall directionality of a portion of the segmentation mask near said image element.

In sub-step 512, a region, here referred to as "first region", of connected candidate image elements is retained among the candidate image elements (determined in sub-step 511). The first region comprises the seed.

In sub-step 513, the retained first region is used to form a new segmentation mask, here referred to as "intermediate segmentation mask".

In sub-step 514, a second region of connected candidate image elements is retained among the candidate image elements (determined in sub-step 511). The second region is not connected to the intermediate segmentation mask (formed in sub-step 513) and is positioned apically (i.e., towards the tip of the tooth root) from the intermediate segmentation mask in a direction consistent with a directionality of an apical portion of the intermediate segmentation mask nearest to the second region. This sub-step enables the addition to the segmentation mask of a region of connected image elements which is separated from the current intermediate segmentation mask. From an anatomical point of view, the separation is typically caused by an occlusion, such as calcification in a root canal. In other words, sub-step 514 enables to pass small canal obstructions caused by calcifications that locally obstruct the canal. In one embodiment, the direction of the segmented root canal is estimated using principal component analysis (PCA).

Then, in sub-step 515, the intermediate segmentation mask and the retained second region are together used to update the segmentation mask.

In one embodiment, sub-step 511 further comprises GT taking as reference the current segmentation mask. Furthermore, in one sub-embodiment, in at least one iteration of the enhanced update procedure 510, an importance or weight associated, for an image element under consideration, to the CBSR relative to the GT increases with increasing distance of the image element from the seed.

Figure 3:
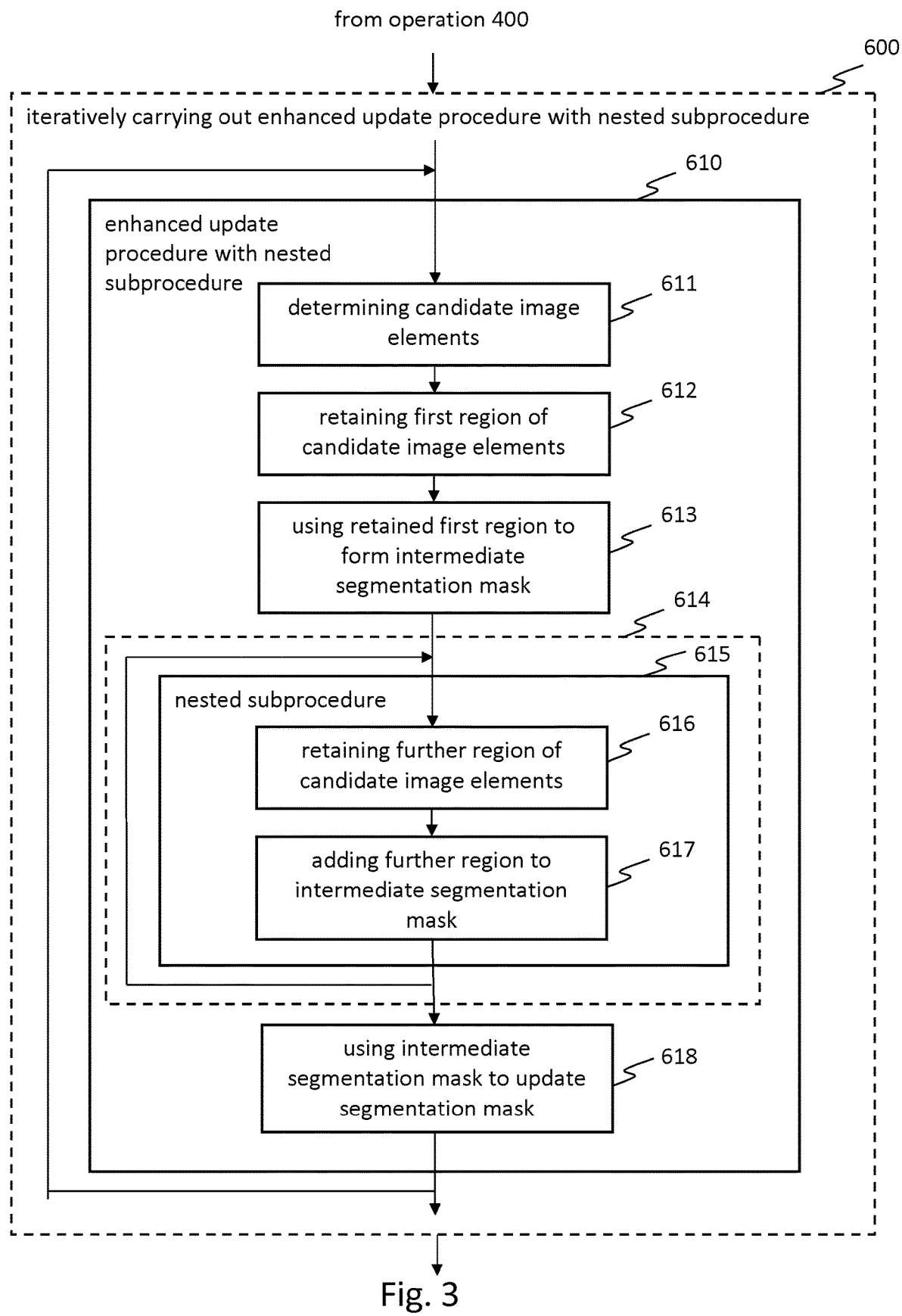
FIG. 3 is a flowchart of a method in one embodiment of the development, further comprising, compared to the flowchart of FIG. 1, iteratively carrying out an enhanced update procedure with a nested subprocedure.

FIG. 3 is a flowchart of a method in one embodiment of the development, comprising iteratively 600 carrying out a further procedure 610, here referred to as "enhanced update procedure with a nested subprocedure". Iteratively carrying out 600 the enhanced update procedure (with a nested subprocedure) 610 is performed after having iteratively carried out 400 the update procedure 410, as illustrated by the mention "from operation 400" on the top of FIG. 3.

The enhanced update procedure (with a nested subprocedure) 610 comprises the following sub-steps:

Sub-steps 611, 612, and 613 are identical to above-described sub-steps 511, 512, and 513 respectively (described with reference to FIG. 2) and will not be described again hereinafter. In the same manner as sub-step 513, sub-step 613 leads to forming an intermediate segmentation mask.

In sub-step 614, a subprocedure 615, here referred to as "nested subprocedure", is iteratively carried out. The nested subprocedure comprises two sub-steps, namely sub-steps 616 and 617. In sub-step 616, a further region of connected candidate image elements is retained among the candidate image elements (determined in sub-step 611). The further region is not connected to the current intermediate segmentation mask (formed either in sub-step 613 or in the previous iteration of the nested subprocedure 615) and is positioned apically from the intermediate segmentation mask in a direction consistent with a directionality of an apical portion of the intermediate segmentation mask nearest to the further region. This process is further explained in section 4.G below. In sub-step 617, the further region is then added to the current intermediate segmentation mask to form a new intermediate segmentation mask.

Sub-step 614 enables the addition to the segmentation mask of further regions of connected image elements which are separated from the segmentation mask containing the seed. As mentioned above, such separation is typically caused by an occlusion, such as calcification in a root canal.

In sub-step 618, the intermediate segmentation mask is then used to update the segmentation mask.

In one embodiment, sub-step 611 further comprises GT taking as reference the current segmentation mask. Furthermore, in one sub-embodiment, in at least one iteration of the enhanced update procedure 610 with nested subprocedure 615, an importance or weight associated, for an image element under consideration, to the CBSR relative to the GT increases with increasing distance of the image element from the seed.

Both the embodiments described with reference to FIGS. 2 and 3 allow for expanding the segmentation mask with image regions that are not directly connected to the segmentation mask, thus enabling to pass calcifications within root canals.

In one embodiment, the segmentation mask may lose image elements from one iteration to the next, meaning that in an iteration of the update procedure an image element included in the segmentation mask from the previous iteration can be discarded from the updated segmentation mask. This enables a flexible self-readjustment of the segmentation mask based on all information contained in the segmentation mask at a given iteration. That is, an image element included in the segmentation mask in iteration i may be discarded in the next iteration i+1. In one sub-embodiment, the segmentation mask may lose image elements from one iteration to the next, and the GT is switched on (such as shown in examples 12 to 17 of Table 1).

In another embodiment, the segmentation mask grows, i.e. is forced to grow, from one iteration to the next.

In one embodiment, in at least one iteration of any one of iteration procedures 400, 500, and 600, image elements at a distance larger than a threshold distance from the current segmentation mask are disregarded. This enables the progressive growth of the segmentation mask.

In one embodiment, any one of iteration procedures 400, 500, and 600 is stopped when the new segmentation mask differs from the current segmentation mask by fewer than m image elements, wherein m is a nonzero positive integer. This provides an effective termination criterion.

In one embodiment, the CBSR comprises identifying shape structures corresponding to possible shapes of a root canal or segment thereof, such as identifying tubular structures and/or identifying sheet-like structures.

In one embodiment, the CBSR comprises computing a tubular shape detection filter for each voxel of the 3D image using a multiscale approach. This generally prevents the segmentation mask from growing outside the teeth region. This tubular shape detection filter may for example be estimated from the ratio of the eigenvalues of the Hessian matrix, as further described below. The smallest eigenvectors of these Hessian matrices indicate the major channel directions of the volume corresponding to the direction of the root canals. These directions are then used as an additional driving force enabling the segmented mask to grow in the direction of the root canals. Thanks to this additional force, small calcifications may be passed in the growing procedure as they do not change the dominant channel direction. When an open apex is present, the driving force of this tubular shape detection filter also stops the growing process, even when the surrounding gray values are comparable (or even lower) to the gray values of the root canal.

In one embodiment, the method further comprises visually rendering an anatomy of the segmented tooth's pulp region. This may for example be performed by means of a user interface such as a computer display.

In one embodiment, to visualize the exact boundaries of the final segmented volume, marching cubes are used on the segmentation mask with a threshold of typically ½.

In one embodiment, the method further comprises determining parameters of an anatomy of the segmented tooth's pulp region, such as determining at least one of: widths along at least one root canal of the segmented tooth's pulp region; a center line of at least one root canal of the segmented tooth's pulp region; and a length of at least one root canal of the segmented tooth's pulp region.

The method may be used for planning an endodontic treatment. Therefore, the development also relates, in some embodiments, to the use of any of the above-described methods for planning an endodontic treatment, such as for root canal cleaning. For example, the method may also be used to suggest appropriate tooling for cleaning a canal. More curved canals require less rigid files. The curviness of a canal can be precomputed and mapped to a list of file types. The determined shape of the root canals may also be used at the top of the tooth to suggest an appropriate shape of the entry hole for the drill and files. Additionally, the determined curvature and shape of the canals may be used to suggest the best entry point and angle for the insertion of the file, such that the latter can be bent as desired during cleaning. This may avoid the creation of so-called ledges, which are the result of erroneously angulated drillings inside the root canal.

In one embodiment, the method further comprises estimating both bright and dark canals in the original image data (e.g., CBCT data). This can be used to segment for example bright root canals that are already treated and filled with gutta-percha. This enables the detection of root canals that are missed in a first endodontic treatment. During such a treatment, the root canals may have been filled with gutta-percha, but one or several canals may have been missed. These root canals may also be segmented to plan the second treatment.

The development further relates, in some embodiments, to a system for segmenting a tooth's pulp region from a 2D or 3D image of said tooth, said system comprising a processing unit configured for performing any of the above-described methods, including at least steps 100, 200, 300, and 400. Yet furthermore, the development further relates to a system for segmenting a tooth's pulp region from a 2D or 3D image of said tooth, said system comprising at least a curvature-based shaped recognition unit for performing step 100, a seed indication receiving unit for performing step 200, a using unit for performing step 300, and an update unit for performing step 400. Furthermore, the development further relates to a computer program comprising computer-readable instructions configured for, when executed on a computer, causing the computer to carry out any of the above-described methods.

Now, further aspects and considerations relating to some embodiments of the development are described, as well as further examples and embodiments thereof, including a first, a second, and a third exemplary sets of embodiments in sections 2, 3, and 4 below, respectively.

Figure 4:
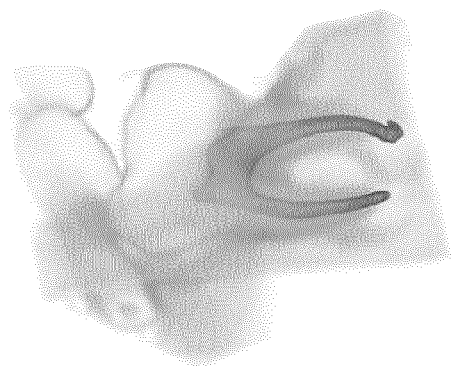
Figure 4:
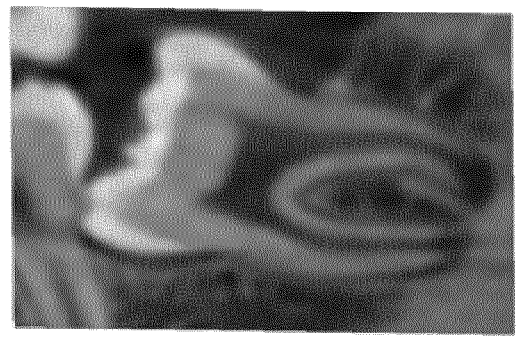
Figure 4:
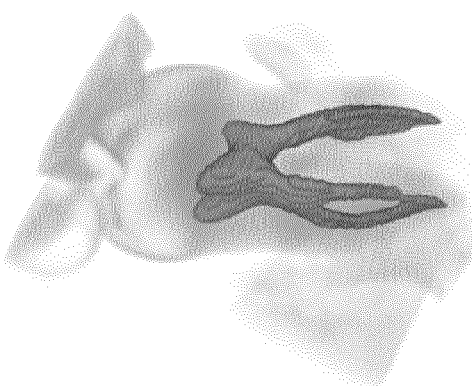
Figure 4:
Figure 4:
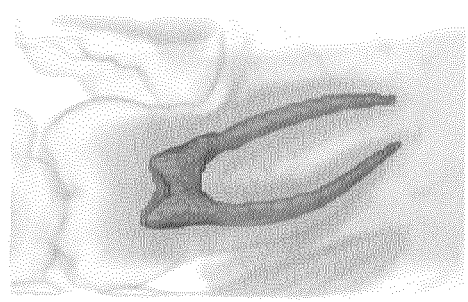
Figure 4:
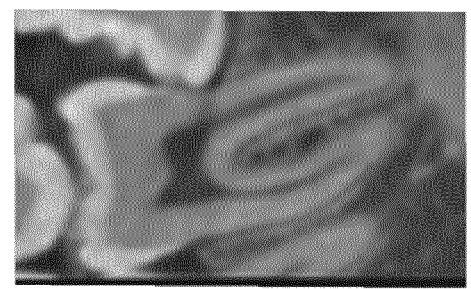

In some embodiments, the method aims at obtaining a complete segmentation of all root canals in CBCT image data starting from a single (e.g., user-selected) seed point in the tooth's pulp chamber. Generally, obtaining such segmentation is not straightforward for several reasons. First, small calcifications inside a root canal may obstruct it. Second, partial volume effects (PVE) may be present due to the limited resolution of the 3D data. As mentioned above, PVE occurs when multiple tissue types are located in the same voxel of the 3D volume yielding gray values that are a mixture of the gray values of the individual tissues. This effect becomes especially important at the narrow tips of the root canals. Third, the potentially intricate shapes of certain root canals should be detected. In some teeth, there are more canals than roots (especially in the molars). Further, a single canal may bifurcate into two parts, and/or merge later on again into one canal. The shape and curvature of the canal also determines the flexibility and length of the files that are used during the treatment. In addition, for children in the age of 7 to 14 years for whom the teeth are not yet fully grown, the root canal may be open at the apices of the teeth. Some embodiments of the development provide a solution capable to segment such cases as well. For three different molars, a 3D visualization of CBCT data of the root canals is shown in FIG. 4, wherein FIGS. 4a to 4c show the 3D visualization of possible root canals, and FIGS. 4d to 4f show 2D slices through the corresponding 3D CBCT volumes. FIGS. 4b and 4e show a case where bifurcations are present inside the root canal. An example of open apices is shown in FIGS. 4c and 4f.

In contrast, the tool of ref. [2] has limitations. First, the root canal detection and segmentation of ref. [2] are time-consuming and subjective due to the manual user interaction, i.e. the considerable input that is manually provided, limiting the reproducibility of the results. Second, effects such as bifurcations (i.e. a split or a merge) or a C-shaped canal may be hard to visualize. This additional information is desirable during endodontic treatment because it influences the instrumentation and methodology used during the procedure. Third, the method ultimately results in only the central or manually indicated line, which is then directly used as file-approximation instead of searching for realistic file trajectories.

1. Some Mathematical Concepts Underlying (CB)CT Scan Data Analysis

Figure 5:
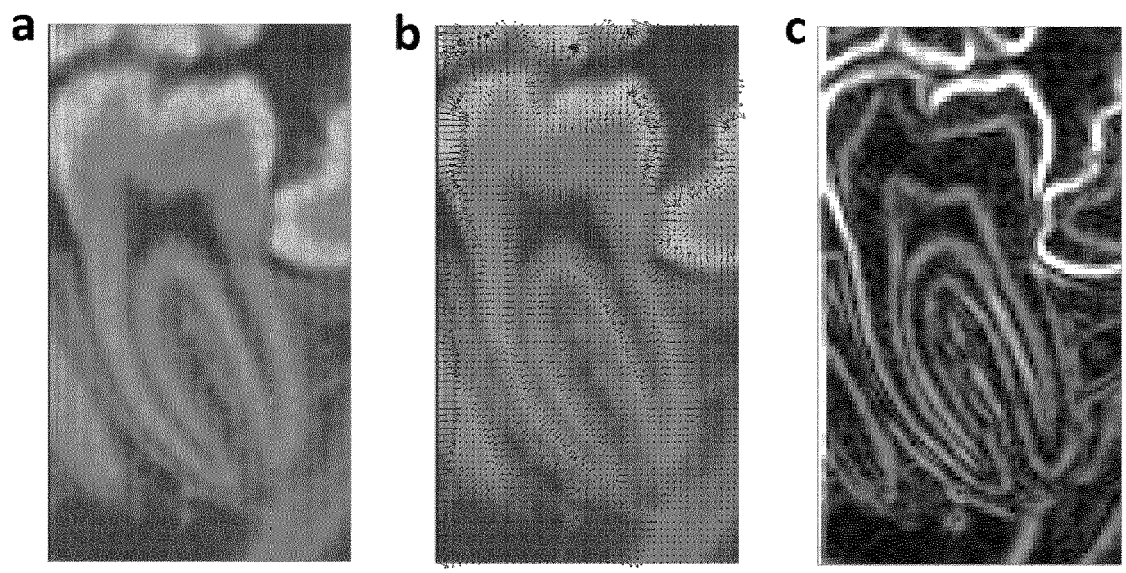
FIG. 5 shows, to assist in understanding some embodiments of the development, examples of: a slice through a 3D scalar CBCT volume (FIG. 5a), a slice through a gradient vector field indicating the directions of the largest variation in gray levels of the original volume (FIG. 5b), and the magnitude of a gradient vector field indicating the edges (FIG. 5c)

The result of a 3D CBCT scan can be considered as a 3D scalar image volume where each voxel at a position (x,y,z) contains a specific value describing the X-ray attenuation by the tissue at that voxel location. Mathematically, this can be described by a 3D intensity function I(x,y,z). An example of a 2D slice through such a 3D volume is shown in FIG. 5a. The image gradient ∇I is defined as a vector field that indicates the direction in which the largest variation of gray values is found (as shown in FIG. 5b). The gradients typically point in the direction of the largest gray value density. Mathematically, it can be computed as:

$$\nabla I(x, y, z) = \frac{\partial I(x, y, z)}{\partial x}, \frac{\partial I(x, y, z)}{\partial y}, \frac{\partial I(x, y, z)}{\partial z} \quad (1)$$

In discrete image space, these derivatives are computed as:

$$\frac{\partial [k, l, m]}{\partial x} = \frac{I(k+1, l, m] - I[k-1, l, m]}{2} \quad (2)$$

$$\frac{\partial [k, l, m]}{\partial y} = \frac{I[k, l+1, m] - I[k, l-1, m]}{2} \quad (3)$$

$$\frac{\partial [k, l, m]}{\partial z} = \frac{I[k, l, m+1] - I[k, l, m-1]}{2} \quad (4)$$

The magnitude of the gradient vector field provides again a scalar field that indicates the object or tissue boundaries. An example is shown in FIG. 5c and mathematically it is defined as:

$$\|\nabla I(x, y, z)\|_2 = \sqrt{\left(\frac{\partial I(x, y, z)}{\partial x}\right)^2 + \left(\frac{\partial I(x, y, z)}{\partial y}\right)^2 + \left(\frac{\partial I(x, y, z)}{\partial z}\right)^2} \quad (5)$$

The second-order derivative of the 3D intensity function I is represented in the so-called Hessian matrix H(x,y,z) which is a square matrix containing all second-order partial derivatives. If the second-order derivatives are continuous, which is generally the case for practical applications, the order of derivatives can be changed and this Hessian matrix is also a symmetric matrix.

$$H(x, y, z) = \begin{bmatrix} \frac{\partial^2 I}{\partial x^2} & \frac{\partial^2 I}{\partial x \partial y} & \frac{\partial^2 I}{\partial x \partial z} \\ \frac{\partial^2 I}{\partial y \partial x} & \frac{\partial^2 I}{\partial y^2} & \frac{\partial^2 I}{\partial y \partial z} \\ \frac{\partial^2 I}{\partial z \partial x} & \frac{\partial^2 I}{\partial z \partial y} & \frac{\partial^2 I}{\partial z^2} \end{bmatrix} \quad (6)$$

In discrete image space, the second derivative is computed as:

$$\frac{\partial^2 [k, l, m]}{\partial x^2} = I[k-1, l, m] - 2I[k, l, m] + I[k+1, l, m] \quad (7)$$

$$\frac{\partial^2 I[k, l, m]}{\partial x \partial y} = \frac{1}{4}(I[k-1, l-1, m] - I[k+1, l-1, m] - I[k-1, l+1, m] + [k+1, l+1, m]) \quad (8)$$

Similar expressions can be found for the other coordinates. These equations correspond to a convolution with stencils:

$$Cxx = [1 \quad -2 \quad 1] \tag{9}$$

$$Cxy = \begin{bmatrix} -\frac{1}{4} & 0 & \frac{1}{4} \\ 0 & 0 & 0 \\ \frac{1}{4} & 0 & \frac{-1}{4} \end{bmatrix} \tag{10}$$

2. First Exemplary Set of Embodiments: Segmentation of the Pulp Region Using Gray Scale Thresholding (GT) and Curvature-Based Shape Recognition (CBSR)

A. Preprocessing the Image Volume

CT or CBCT image data for use in a segmentation method in some embodiments of the development comprises data on a tooth under investigation. The image data may for example be subjected to following pre-processing steps.

i. Cropping

As the pulp region is fully contained in a tooth, it is generally desirable to crop the (CB)CT volume to the region of interest (ROI), being the region comprising the entire tooth under investigation.

ii. Resizing Voxel Size

Endodontic (CB)CT data may for example have a voxel size equal to 0.2 mm. If image data with a smaller voxel size are used, this may drastically increase the computation time of the segmentation process. Therefore, it is generally desirable to resize such data sets to a voxel size of 0.2 mm by averaging the gray values into cubes with a side of 0.2 mm. As part of the development of some embodiments of the development, it was found that a voxel size of 0.2 mm generally provides sufficient resolution for studying the pulp region.

iii. Rescaling Gray Values

It is generally desirable to rescale the gray values to the range [0, 1] in a further pre-processing step. Mathematically, rescaling the gray values from the initial volume $I_{orig}$ corresponds to:

$$I_{new}(r) = \frac{I_{orig}(r) - I_{min}}{I_{max} - I_{min}} \tag{11}$$

Here, $I_{new}(r)$ corresponds to the resealed gray value for a given voxel and $I_{orig}(r)$ corresponds to the original gray value for this voxel. $I_{min}$ and $I_{max}$ are the minimum and maximum intensity levels of the original image volume.

B. Initializing the Segmentation Mask

The initial segmentation mask $S_0$ is set based on a received indication of a point or region assumed to be located in the imaged pulp chamber of the tooth (steps 200, 300, as described above). This point or region may be indicated by a user or may be automatically generated by a computer or the like.

In a segmentation procedure according to some embodiments, the segmentation mask may be initialized by setting the segmentation mask value S(r) for the voxel (referred to as seed voxel) corresponding to the position of the initial seed point together with that of selected neighboring voxels (resulting for instance in a cubic region of 5×5×5 voxels) to 1 and to 0 for all other voxels. In some embodiments, when the initial segmentation mask comprises a region surrounding a seed point voxel, the seed point is desirably located at a minimum distance from the edges of the pulp chamber, for instance at a distance of at least 2, 3 or 4 voxels from the closest pulp chamber edge. The initial segmentation mask is subsequently iteratively updated to segment the pulp region (step 400). Throughout the present description, the initial segmentation mask and the respective updated segmentation masks are also referred to simply as segmentation masks.

C. Computing Curvature-Based Shape Recognition (CBSR) Terms (Also Referred to as Object Feature Detection Term) (Step 100)

As part of the development of some embodiments of the development, it was observed that the canal segments of the pulp region typically have a tubular or sheet-like shape (see for example FIG. 4). Thus, the presence of a voxel in a dark tubular or sheet-like shape is indicative that this voxel is located within a root canal. Therefore, using the pre-processed image data, CBSR terms may be computed for each voxel. More particularly, a tubular shape detection filter value C(r) and a sheet-like shape detection filter value P(r) may be computed for each voxel using a multiscale approach, for instance using different 3D Gaussian stencils with varying scale factors σ (see also below).

For computing the C(r) and P(r) values, the original volume may be blurred using a 3D Gaussian stencil as an exemplary form of generation of a smoothed version of the image. Then, the Hessian matrix may be computed using equations (6) to (8) and a fixed-step size for the Hessian using nearest neighbour finite differences. The diagonal elements of the Hessian matrix are large when the shape to be detected has a high curvature along the corresponding principle axes. To find object features that are located along arbitrary directions, the eigenvalues and eigenvectors of the Hessian matrix are computed. If $\lambda_1$, $\lambda_2$ and $\lambda_3$ are the eigenvalues of the Hessian matrix H with corresponding eigenvectors $v_1$, $v_2$ and $v_3$, the Hessian matrix may be decomposed using the eigenvalue decomposition:

$$H = V \Sigma V^T \tag{12}$$

Here, Σ is a diagonal (3×3) matrix containing the eigenvalues, and V is a matrix with the corresponding eigenvectors as its columns. These eigenvectors form an orthonormal basis that is aligned with the object along the directions of the main curvature. Intuitively, a large eigenvalue corresponds to an eigenvector direction where a large curvature is present in the profile of the smoothed volume, whereas a small eigenvalue corresponds to an eigenvector direction where the volume remains almost constant. The eigenvalues of the Hessian matrix are desirably computed for each voxel inside the 3D volume. If the eigenvalues are sorted based on their absolute values so that $||\lambda_1|<|\lambda_2|<|\lambda_3|$, different object features may be detected based on the eigenvalue analysis of the Hessian matrices as for example shown in Table 2.

TABLE 2

Possible object features in 3D volumes, depending on the value of the eigenvalues. The eigenvalues are ordered so that $|\lambda_1| < |\lambda_2| < |\lambda_3|$.

| λ1 | λ2 | λ3 | Object feature |
|---|---|---|---|
| L | L | L | noise |
| L | L | H− | sheet-like structure (bright) |
| L | L | H+ | sheet-like structure (dark) |
| L | H− | H− | tubular structure (bright) |
| L | H+ | H+ | tubular structure (dark) |

TABLE 2-continued

Possible object features in 3D volumes, depending on the value of the eigenvalues. The eigenvalues are ordered so that $|\lambda_1| < |\lambda_2| < |\lambda_3|$.

| λ1 | λ2 | λ3 | Object feature |
|----|----|----|----------------|
| H− | H− | H− | blob-like structure (bright) |
| H+ | H+ | H+ | blob-like structure (dark) |

(H = high value, L = low value, + and − indicate the sign of the eigenvalue).

Detection of Tubular Shapes in 3D Volumes:

As illustrated in Table 2, for a voxel within a dark tubular shape inside a 3D volume, two large positive eigenvalues and a small eigenvalue are generally found. The direction of the eigenvector corresponding to the smallest eigenvalue is directed along the axis of the tubular shape where there is no curvature, whereas the other two eigenvectors are perpendicular to this axis. In these two directions, a high curvature is present in the 3D volume. As measures for the detection of a voxel in dark tubular shape, ratios of the absolute values of the eigenvalues may be used. Because there is one small eigenvalue $\lambda_1$ and two large ones, $\lambda_2$ and $\lambda_3$, the ratios $$R_{12} = \frac{\lambda_1}{\lambda_2} \text{ and } R_{13} = \frac{\lambda_1}{\lambda_3}$$

are small as well. In addition, the norm of all eigenvalues defined as $=\sqrt{\lambda_1^2+\lambda_2^2+\lambda_3^2}$ is used to discriminate between a channel object and noisy background signals (see table 2). The tubular shape detection filter value $C_\sigma(r)$, which is computed on the smoothed volume $G_\sigma*I(r)$ (i.e., product of Gaussian with standard deviation a by image data $I(r)$) to detect dark tubular shapes with a width of $2\sigma$, may then be defined for example as:

$$C\sigma(r) = \begin{cases} 0 & \text{if } \lambda 2 < 0 \text{ or } \lambda 3 < 0 \\ \exp\left(-\frac{R_{12}^2}{2\alpha^2}\right)\exp\left(-\frac{R_{13}^2}{2\alpha^2}\right)\left(1-\exp\left(-\frac{L^2}{2\beta^2}\right)\right) & \text{otherwise} \end{cases} \quad (13)$$

This may be computed for every voxel at position r=(x, y,z). Parameters, α and β were empirically determined. In the present examples, satisfactorily results were obtained when the parameter α was set to 0.5, and the parameter β was set to twice the mean of L over the image data.

Detection of Sheet-Like Structures in 3D Volumes:

Although the detection of tubular structures inside a 3D volume is particularly useful for the detection of voxels of root canal segments in image data of both incisors and molars, it has been found as part of the development of some embodiments of the development that root canals of molars often have segments with a sheet-like shape (see the right root canal in FIG. 4b as an example). For a dark sheet-like structure, Table 2 prescribes that two small eigenvalues, $\lambda_1$ and $\lambda_2$, are present and one large positive eigenvalue $\lambda_3$. The eigenvector corresponding to this largest eigenvalue is directed perpendicular to the sheet, while the other two eigenvectors are perpendicular to this largest eigenvector and point along the plane of sheet. Similarly to the tubular shape detection filter, the ratios may for example be defined as $$R_{13} = \frac{\lambda_1}{\lambda_3} \text{ and } R_{23} = \frac{\lambda_2}{\lambda_3},$$

and the sheet-like shape detection filter $P_\sigma(r)$ for a voxel in a dark sheet with a width of $2_\sigma$ may for example be computed as follows:

$$P\sigma(r) = \begin{cases} 0 & \text{if } \lambda 3 < 0 \\ \exp\left(-\frac{R_{13}^2}{2\alpha^2}\right)\exp\left(-\frac{R_{23}^2}{2\alpha^2}\right)\left(1-\exp\left(-\frac{L^2}{2\beta^2}\right)\right) & \text{otherwise} \end{cases} \quad (14)$$

A Multiscale Approach to the CBSR Term:

Equations (13) and (14) allow computing for every voxel in the 3D volume a value which represents the likelihood that this voxel is present in a tubular or sheet-shaped structure, respectively. However, the computation was presented so far for a specific scale a, which is determined by the 3D Gaussian function that is used to smooth the original volume. In order to detect object features at multiple scales, a multiscale approach is used wherein both $C_\sigma(r)$ and $P_\sigma(r)$ may be computed for multiple scales a. The maximum value of each of $C_\sigma(r)$ and $P_\sigma(r)$ may be kept for each voxel:

$$C(r) = \max_{\sigma_{min} \leq \sigma \leq \sigma_{max}} C\sigma(r) \quad (15)$$

$$P(r) = \max_{\sigma_{min} \leq \sigma \leq \sigma_{max}} P\sigma(r) \quad (16)$$

In an exemplary embodiment, $\sigma_{min}=0$ and $\sigma_{max}=0.6$ mm and the step size $\Delta\sigma=0.1$ mm.

Figure 6:
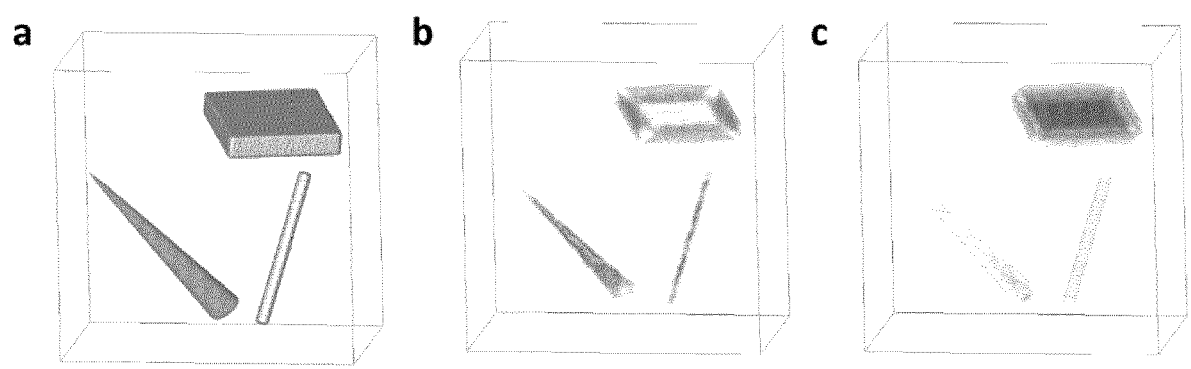
FIG. 6 shows, to assist in understanding some embodiments of the development, examples of: a 3D volume containing multiple object features (FIG. 6a), an output of a tubular shape detection filter C(r) (FIG. 6b), and an output of a sheet-like shape detection filter P(r) (FIG. 6c)

An example of a 3D volume containing different shapes is provided in FIG. 6, where the original volume is shown in FIG. 6a, the output of the tubular shape detection filter C(r) is shown in FIG. 6b, and the output of the sheet-like shape detection filter P(r) is shown in FIG. 6c. The curvature-based shape recognition (CBSR) terms in this example were calculated using the above-explained multi-scale approach. The advantage of the multi-scale approach is illustrated by the cone shape. Although the dimensions of the cone vary along its axis, the tubular shape detection filter detects both the image elements at the cone basis as well as those near the tip as being positioned in a tubular shape.

Figure 7:
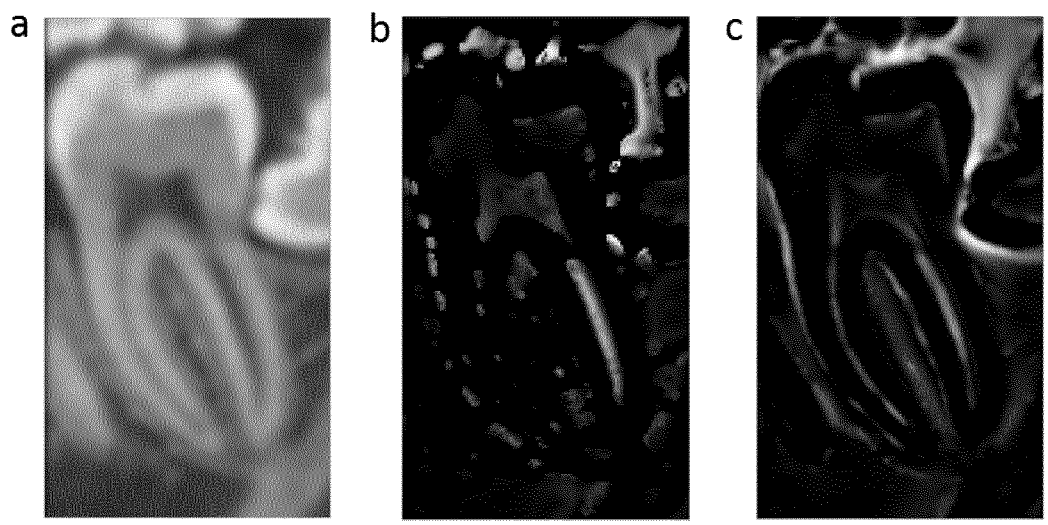
FIG. 7 shows, to assist in understanding some embodiments of the development, examples of: a slice through an original 3D CBCT image (FIG. 7a), an output of a tubular shape detection filter C(r) (FIG. 7b), and an output of a sheet-like shape detection filter P(r) (FIG. 7c)

An example of a tooth with two root canals, one of them being more sheet-like (left canal) and the other being more tube-like (right canal), is shown in FIG. 7. FIG. 7a shows a slice through the original 3D volume, whereas FIGS. 7b and 7c show the result of a tubular shape detection filter and a sheet-like shape detection filter, respectively. FIG. 7 shows that canal regions of a pulp region can be detected by either a sheet-like shape detection filter or a tubular shape detection filter. The curvature-based shape recognition (CBSR) terms in the example represented in FIG. 7 were determined using the above-explained multi-scale approach allowing for variations of the width of the root canal.

D. Gray Value Thresholding or Grayscale Thresholding (GT) (Part of Step 411)

In some embodiments, for all voxels with a gray value I(r), the darkness contribution G(r) is computed as follows using the current segmentation mask S(r) as available in a given iteration:

$$G(r)=(I(r)-c_1(r))^2+(I(r)-c_2(r))^2 \quad (17)$$

Here, $c_1(r)$ and $c_1(r)$ are the averaged foreground (segmented root canal) and background (not segmented region) intensity values that are computed in the neighborhood of r based on the current segmentation mask. Mathematically this may be written for example as (see also ref. [5]):

$$c_1(r) = \frac{\int I(r')S(r')B(r, r')dr'}{\int S(r')B(r, r')dr'} \quad (18)$$

$$c_2(r) = \frac{\int I(r')(1 - S(r'))B(r, r')dr'}{\int (1 - S(r'))B(r, r')dr'} \quad (19)$$

Here, $B(r,r')$ is a normalized Gaussian function with a standard deviation (a) of for instance 0.8 mm, centered around point r and evaluated at position r'. In some embodiments, after a first n (for example n=3, 4, 5, 6 or 7) iteration of the update procedure 410 of the segmentation mask (see also section 2.E below), the resulting segmentation mask is assumed to encompass the entire pulp chamber. Thereafter, the standard deviation σ in the computation of $c_2(r)$ may optionally be lowered, for instance halved. This advantageously allows avoiding the averaging of the dark region surrounding the tooth with the bright enamel in the direct background of the root canal, resulting in too low $c_2(r)$ values for relevant gray scale thresholding.

In some embodiments, equations (18) and (19) are computed by a discretized Gaussian stencil which is used to filter both the segmentation mask $S(r)$ and the masked volume $I(r)S(r)$.

$$c_1(r) = \frac{\Sigma[I(r')B(r, r') | S(r') = 1]}{\Sigma[B(r, r') | S(r') = 1]} \quad (20)$$

$$c_2(r) = \frac{\Sigma[I(r')B(r, r') | S(r') = 0]}{\Sigma[B(r, r') | S(r') = 0]} \quad (21)$$

The local computation of the average fore- and background gray values $c_1(r)$ and $c_2(r)$ in the gray value thresholding (GT) contributes to the segmentation of the pulp region even when partial volume effects (PVE) are present. When inspecting equation (17), it is seen that, for each voxel, the darkness term $G(r)$ is positive when the intensity level $I(r)$ is closer to the local average foreground value $c_1(r)$ than to the local average background value $c_2(r)$.

For the voxels where the denominator of either $c_1(r)$ or $c_2(r)$ equals zero, the local mean foreground or background value may for example be replaced by $10^6$ as an approximation of infinity. These voxels are respectively remote of any foreground or background voxels and can themselves not be classified as respectively foreground or background voxels, which is indeed avoided with a large value for respectively $c_1(r)$ or $c_2(r)$.

Alternatively, the darkness term $G(r)$ may be computed using an m-estimator instead of the squared estimator of equation (17). For instance, the Welsch estimator as described in ref. [6] can be used wherein:

$$W(s) = \frac{k^2}{2}\left(1 - \exp\left(-\left(\frac{s}{k}\right)^2\right)\right) \quad (22)$$

When using the Welsh estimator, the expression for the darkness term $G(r)$ becomes:

$$G(r) = \frac{k^2}{2}\left[\exp\left(-\frac{(I(r) - c_1(r))^2}{k^2}\right) - \exp\left(-\frac{(I(r) - c_2(r))^2}{k^2}\right)\right] \quad (23)$$

Parameter k was empirically determined. In the present examples, satisfactorily results were obtained with parameter k set at a value comprised between 0.3 and 0.8, such as 0.5.

E. Combining Terms and Updating the Segmentation Mask (Step 400)

In some embodiments, after the darkness term $G(r)$ (representing the result of the GT process) has been computed for all voxels in a given iteration, the darkness term $G(r)$ may be used independently or in combination with curvature-based shape recognition (CBSR) terms to identify the voxels, i.e. the candidate image elements, for updating the segmentation mask of the previous iteration.

It has been found as part of the development of some embodiments of the development that the pulp chamber is typically well segmented using primarily the darkness term $G(r)$. Therefore, in some embodiments, more weight is assigned to the darkness term $G(r)$ for voxels assumed to be in the pulp chamber, while more weight is assigned to the CBSR terms for voxels assumed to be in one of the root canals. This may be achieved by using only or mainly the darkness term $G(r)$ in the initial n iterations, wherein n may for example be set at a value comprised between 1 and 8, such as at a value comprised between 3 and 6, for instance at 5. Alternatively, or in addition, a weight factor $w(r)$ may be used. The weight factor $w(r)$ may be derived from the distance from the original seed point that is assumed to be located in the pulp chamber. First, a 3D distance map $d(r)$ is computed with respect to this seed point. The weight factor $w(r)$ may then be defined for example as the sigmoid function of the 3D distance map:

$$w(r) = 1 - \frac{1}{1 + \exp\left(-\frac{d(r) - b}{a}\right)} \quad (24)$$

For example, the values of a and b may be set as follows: a=2 mm and b=5 mm. When using this weight factor $w(r)$, the update function $U(r)$ for the current iteration may then be defined as the weighted sum of the darkness term $G(r)$ and the shape feature term $R(r)$, which corresponds to the maximum value of the $C(r)$ and $P(r)$ values:

$$R(r) = \max(C(r), P(r)) \quad (25)$$

$$U(r) = w(r)G(r) + (1 - w(r))R(r) \quad (26)$$

After the update values $U(r)$ have been computed using equation (26) in a given iteration, the segmentation mask may be updated (step 413) by including therein the region of connected voxels having a positive $U(r)$ value (for example $U(r) > 10^{-4}$ is used to avoid noise effects) that comprises the seed voxel. The voxels having a positive $U(r)$ value are a form of candidate image elements according to step 411. The region of connected voxels having a positive $U(r)$ value that comprises the seed voxel is a form of region retained according to step 412.

F. Termination of the Segmentation (Termination of Iterative Process According to Step 400)

It has been found that the iterative process 400 typically converges after about ten iterations of update procedure 410. In some embodiments, whether the process 400 has converged may be decided by using a tolerance value v, wherein the segmentation is considered as converged when, in an iteration, fewer than v voxels are added to or removed from the segmentation mask as compared to any one of the previous iterations of update procedure 410, or, alternatively, compared to the previous iteration of update procedure 410. The tolerance value v may for example be set at a value comprised between 1 and 100, such as a value comprised between 2 and 30 or a value comprised between 5 and 25. In some embodiments, the segmentation mask of the last iteration of update procedure 410 is used as the final segmentation result.

In some embodiments, as a failsafe, a maximal number of iterations ($k_{max}$) may be set, wherein ($k_{max}$) may for instance be set at 35. The segmentation mask of the ($k_{max}^{th}$) iteration may then be used as the final segmentation result.

In some embodiments, as a further failsafe and to avoid a rarely occurring excessive over-segmentation, a segmentation mask update is rejected if there is a sudden large increase in the number of added voxels. For instance, the segmentation process 400 may be terminated in the event that the number of added voxels is larger than ten times the number of voxels added in a previous iteration of update procedure 410, and the segmentation mask of the previous iteration is then used as the segmentation result.

A segmentation process according to an embodiment of the first exemplary set of embodiments may be further explained as follows:

Segmentation Process for Root Canal Detection in an Embodiment of the First Exemplary Set of Embodiments.

E. Identifying the Directionality of Recognized Shapes in Relation to that of the Segmentation Mask In some embodiments, the segmentation process exploits the inherent directionality of root canals during the segmentation. This directionality is reflected in the characteristic eigenvectors that belong to the voxels of the current segmentation mask S(r).

When assessing directionality, it is first determined for each voxel in the 3D volume whether this voxel has a tubular or sheet-like character by comparing the output of both tubular and sheet-like shape detection filter values for this voxel. If C(r)≥P(r), the character of voxel r is considered to be tubular. Otherwise, i.e., if C(r)<P(r), the character is considered to be sheet-like. Characters are summarized in the binary 3D matrix $K_{char}(r)$ with the value "1" representing a tubular character and the value "0" representing a sheet-like character. For voxels with a tubular character, the eigenvector corresponding to the smallest eigenvalue is the most characteristic, while, for voxels with a sheet-like character, the eigenvector corresponding to the largest eigenvalue is retained as characteristic eigenvector. During segmentation, the direction of the characteristic eigenvector of every voxel r of the image is compared with the average direction of the characteristic eigenvectors of all the voxels in a region of the segmentation mask near r. For each of the voxels r' within this region of the segmentation mask that has the same character as the current voxel r, the angle α(r,r') between the characteristic eigenvectors for both voxels should be close to zero. For each voxel r' having an opposing character, the angle r should be close to 90°.

Neither the eigenvectors themselves nor the angles α(r,r') can be averaged, as they may be antiparallel (parallel vectors but opposite directions) to others, meaning that the average vector could be zero. This is for example shown in FIG. 8 where it can be seen that some eigenvectors in the root canal point downwards along the canal direction whereas other eigenvectors point upwards along the canal direction. To

---

```
 1:  User selects a seed point in the pulp chamber (step 200).
 2:  Initialize segmented mask S₀(r) based on the seed point (step 300).
 3:  Compute C(r), P(r) and R(r) using equations (15), (16) and (25) (step 100).
 4:  Compute gray level weight w(r) using equation (24).
 5:  For k = 1, ..., k_max
 6:      Compute c₁(r) and c₂(r) using equations (18) and (19) (step 411).
 7:      Compute darkness term G(r) using equation (23) (step 411).
 8:      Compute update function U_k(r) using equation (26) (step 411).
 9:      Update segmentation mask S_k(r) by including the region of connected voxels
         with positive U_k(r) that comprises the seed voxel (steps 411 to 413).
10:      if min_{l=1:k−1}(Σ|S_k(r) − S_l(r)|) ≤ v
11:         Stop.
12:      end
13:  end
```

---

3. Second Exemplary Set of Embodiments: Segmentation of the Pulp Region Using Gray Scale Thresholding (GT) and Curvature Based Shape Recognition (CBSR), Including the Directionality of the Recognized Shapes A. Preprocessing the Image Volume May for example be as explained in section 2.A.

B. Initializing the Segmentation Mask

May for example be as explained in section 2.B.

C. Computing Curvature-Based Shape Recognition (CBSR) Terms (Also Referred to as Object Feature Detection Term) (Step 100)

May for example be as explained in section 2.C.

D. Gray Value Thresholding (GT) (Part of Step 411)

May for example be as explained in section 2.D.

remedy this, the average over r' of the squared cosine of angle α(r,r') or α(r,r')−90° (for corresponding or opposing characters respectively) may for example be computed, which should be close to 1 for both parallel and antiparallel vectors. Mathematically, this may be computed as:

$$A_c(r) = \langle \cos^2 \alpha(r) \rangle \quad (27)$$

$$= \frac{\int \cos^2 \alpha(r, r') B(r, r') S(r') dr'}{\int B(r, r') S(r') dr'} \quad (28)$$

$$= \frac{\int [v_x(r) v_x(r') + v_y(r) v_y(r') + v_z(r) v_z(r')]^2 B(r, r') S(r') dr'}{\int B(r, r') S(r') dr'} \quad (29)$$

-continued $$= v_x^2(r)\langle v_x^2(r)\rangle + v_y^2(r)\langle v_y^2(r)\rangle + v_z^2(r)\langle v_z^2(r)\rangle + 2v_x(r)v_y(r)\langle v_x(r)v_y(r)\rangle + \qquad (30)$$
$$2v_x(r)v_z(r)\langle v_x(r)v_z(r)\rangle + 2v_y(r)v_z(r)\langle v_y(r)v_z(r)\rangle$$

$$A_o(r) = \langle \cos^2\alpha(r) - 90°\rangle \qquad (31)$$

$$= \langle \sin^2\alpha(r)\rangle \qquad (32)$$

$$= \frac{\int \sin^2\alpha(r, r')B(r, r')S(r')dr'}{\int B(r, r')S(r')dr'} \qquad (33)$$

$$= \int [(v_x(r)v_y(r') - v_y(r)v_x(r'))^2 + (v_y(r)v_z(r') - v_z(r)v_y(r'))^2 + \qquad (34)$$
$$(v_z(r)v_x(r') - v_x(r)v_z(r'))^2]\frac{B(r, r')S(r')dr'}{\int B(r, r')S(r')dr'}$$

$$= v_x^2(r)\langle v_y^2(r) + v_z^2(r)\rangle + v_y^2(r)\langle v_x^2(r) + v_z^2(r)\rangle + \qquad (35)$$
$$v_z^2(r)\langle v_x^2(r) + v_y^2(r)\rangle - 2v_x(r)v_y(r)\langle v_x(r)v_y(r)\rangle -$$
$$2v_x(r)v_z(r)\langle v_x(r)v_z(r)\rangle - 2v_y(r)v_z(r)\langle v_y(r)v_z(r)\rangle$$

Here $[V_x(r), V_y(r), V_z(r),]$ is the normalized characteristic eigenvector in voxel r and $\langle \bullet \rangle$ denotes the average value for the voxels in the segmentation mask within the neighbourhood of r. This neighbourhood is defined by a Gaussian stencil B(r,r') with a standard deviation of for instance 0.8 mm. This may for example be computed as:

$$\langle f(r)\rangle = \frac{\Sigma[f(r)B(r, r') \mid S(r') = 1]}{\Sigma[B(r, r') \mid S(r') = 1]} \qquad (36)$$

Figure 8:
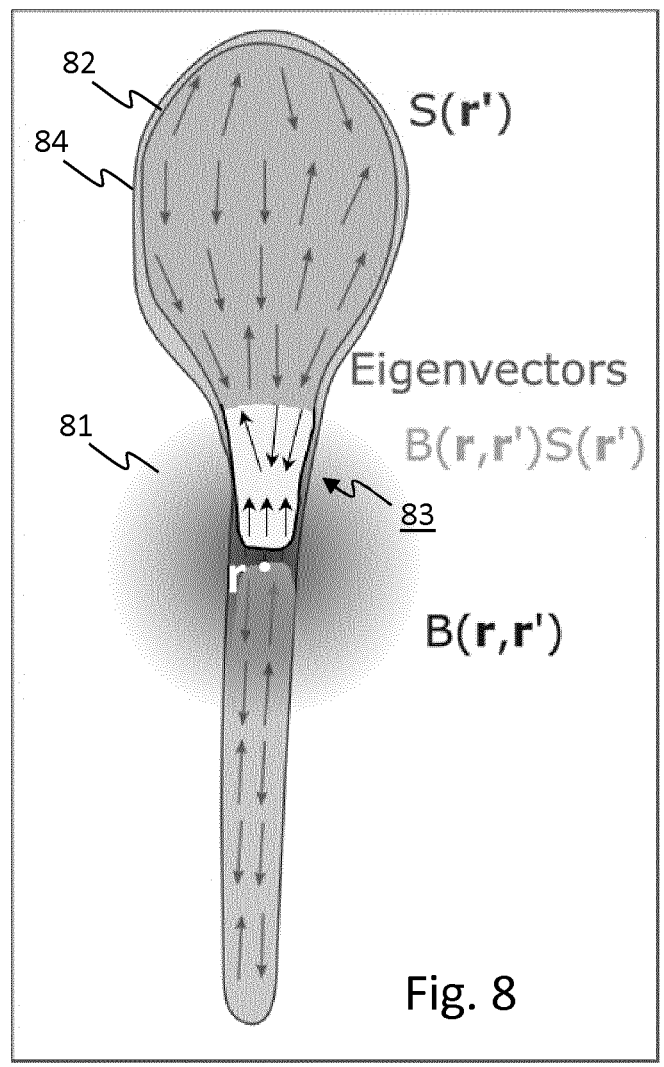
FIG. 8 shows, to assist in understanding some embodiments of the development, examples of how the directionality of characteristic eigenvectors may be included in object feature filters.

When the denominator of this expression equals zero, the average value is replaced by the value 0. A graphical illustration of this equation is shown in FIG. 8, wherein the elongated gray shape 84 schematically represents the pulp region (broader upper part: pulp chamber; narrower lower part: root canal) to be segmented. The eigenvectors computed at all voxels are represented by the arrows. The gray disk 81 partially overlaying the pulp region 84 and centered around point r represents the Gaussian stencil B(r,r') around the voxel position r. The current segmentation mask S(r') is the upside-down-pear-shaped region 82 depicted above point r and having a solid-line contour, and the grayish-white region 83 represents the Gaussian function evaluated in the segmentation mask 82. That is, the product B(r,r')S(r') of Gaussian stencil 81 and the current segmentation mask 82 is represented by the grayish-white region 83. If voxel r has a tubular character, functions $A_c(r)$ and $A_o(r)$ (for voxels with corresponding and opposing character respectively) may be combined to: Text use $$A_t(r) = v_x^2(r)\langle v_x^2(r)\cdot K_{char}(r) + (v_y^2(r) + v_z^2(r))\cdot(1 - K_{char}(r))\rangle + v_y^2(r)\langle v_y^2(r)\cdot K_{char}(r) + (v_x^2(r) + v_z^2(r))\cdot(1 - K_{char}(r))\rangle + v_z^2(r)\langle v_z^2(r)\cdot K_{char}(r) + (v_x^2(r) + v_y^2(r))\cdot(1 - K_{char}(r))\rangle + 2v_x(r)v_y(r)\langle v_x(r)v_y(r)\cdot(2K_{char}(r) - 1)\rangle + 2v_y(r)v_z(r)\langle v_y(r)v_z(r)\cdot(2K_{char}(r) - 1)\rangle + 2v_x(r)v_z(r)\langle v_x(r)v_z(r)\cdot(2K_{char}(r) - 1)\rangle \qquad (37)$$

If voxel r has a sheet-like character, functions $A_c(r)$ and $A_o(r)$ may be combined to:

$$A_t(r) = v_x^2(r)\langle v_x^2(r)\cdot(1 - K_{char}(r)) + (v_y^2(r) + v_z^2(r))\cdot K_{char}(r)\rangle + v_y^2(r)\langle v_y^2(r)\cdot(1 - K_{char}(r)) + (v_x^2(r) + v_z^2(r))\cdot K_{char}(r)\rangle + v_z^2(r)\langle v_z^2(r)\cdot(1 - K_{char}(r)) + (v_x^2(r) + v_y^2(r))\cdot K_{char}(r)\rangle + 2v_x(r)v_y(r)\langle v_x(r)v_y(r)\cdot(1 - 2K_{char}(r))\rangle + 2v_y(r)v_z(r)\langle v_y(r)v_z(r)\cdot(1 - 2K_{char}(r))\rangle + 2v_x(r)v_z(r)\langle v_x(r)v_z(r)\cdot(1 - 2K_{char}(r))\rangle \qquad (38)$$

So finally, the total function A(r) may be written as:

$$A(r) = A_t(r)\cdot K_{char}(r) + A_s(r)\cdot(1 - K_{char}(r)) \qquad (39)$$

Figure 9:
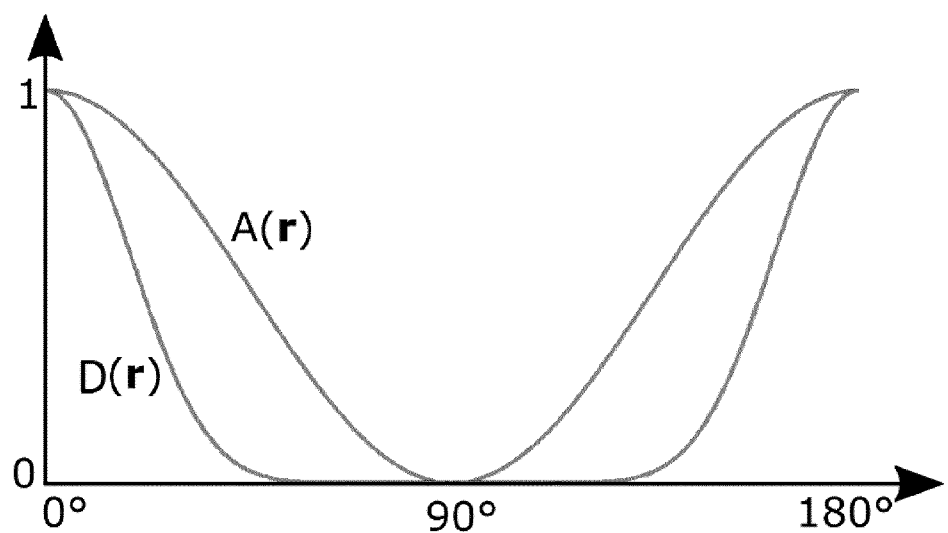
FIG. 9 shows, to assist in understanding some embodiments of the development, a total function A(r) and a directionality function D(r)

The profile of A(r) is plotted in FIG. 9. When inspecting this graph, it can be noticed that there is still a considerable contribution even when the angle of the characteristic vector of a voxel r with the average direction of the characteristic eigenvectors of the voxels in a region of the segmentation mask near r is relatively far from 0° or 180°. Therefore, a so-called directionality function $D(r) = A^5(r)$ may be used. As shown in FIG. 9, this directionality function D(r) decreases much faster once the angle deviates from 0° or 180° which is the desired behavior.

Thus, in this example, the tubular and sheet-like measurements C(r) and P(r) are multiplied in one or more iterations with the directionality function D(r), which is computed based on the segmentation mask, in order to take the directionality of the characteristic eigenvectors into account.

$$\hat{C}(r) = C(r)D(r) \qquad (40)$$

$$\hat{P}(r) = P(r)D(r) \qquad (41)$$

The filter values $\hat{C}(r)$ and $\hat{P}(r)$ of equations (40) and (41) may be combined in one object feature term O(r) for every voxel r of the 3D volume:

$$O(r) = \hat{C}(r)\cdot K_{char}(r) + \hat{P}(r)(1 - K_{char}(r)) \qquad (42)$$

The resulting 3D image volume may be normalized between 0 and 1. This object feature filter O(r) yields a volume where the values indicate the presence of relevant object features.

Similarly to the darkness term G(r) of equation (23), an object feature term F(r) may be defined which is positive for voxels that correspond more to the average object featureness of the region of the segmentation mask neighboring said voxel (foreground) and negative for voxels that correspond better to the average object featureness of the nearby region outside the segmentation mask (background).

$$F(r) = \frac{k^2}{2}\left[\exp\left(-\frac{(O(r) - d_1(r))^2}{k^2}\right) - \exp\left(-\frac{((O(r) - d_2(r))f_s)^2}{k^2}\right)\right] \qquad (43)$$

with $$k = 0.5$$

Also for the object featureness, it is desirable, in some embodiments, to use a more robust m-estimator instead of the squared estimator, such as the robust Welsch estimator as defined in equation (22).

Here, $d_1(r)$ and $d_2(r)$ are the averaged foreground (within the segmentation mask) and background (outside the segmentation mask) object featureness values that are computed in the neighborhood of r based on the current segmentation mask and are computed as follows:

$$d_1(r) = \frac{\Sigma[O(r')B(r, r') \mid S(r') = 1]}{\Sigma[B(r, r') \mid S(r') = 1]} \qquad (44)$$

-continued $$d_2(r) = \frac{\Sigma[O(r')B(r, r') \mid S(r') = 0]}{\Sigma[B(r, r') \mid S(r') = 0]} \quad (45)$$

For voxels for which the denominator of either $d_1(r)$ or $d_2(r)$ equals zero, the local foreground or background value, respectively, is replaced by $10^6$.

The featureness sensitivity factor s in equation (43) allows for the setting of a cut-off between the fore- and background that is not necessarily halfway between $d_1(r)$ and $d_2(r)$. For example, featureness sensitivity factor f may be set at 1. However, in some embodiments, featureness sensitivity factor f may be set at a value being larger than 1, such as for example 1.5 or 2, to also include voxels with less pronounced featureness in the canal segmentation.

F. Combining Terms and Updating the Segmentation Mask

Once both the darkness term G(r) and the object feature term F(r) have been computed, they may be combined to update the previous segmentation mask.

The object feature term F(r) is mainly positive inside the root canal sections of the pulp region whereas the pulp chamber is not well indicated by this term. It has been found that the pulp chamber is typically well segmented using primarily the darkness term G(r). Therefore, it is advantageous to give the darkness term G(r) more weight for voxels assumed to be in the pulp chamber, while assigning more weight to the object feature term F(r) for voxels assumed to be in one of the root canals. This may be achieved by using only or mainly the darkness term G(r) in the initial n iterations, wherein n may for example be set at a value comprised between 1 and 8, such as at a value comprised between 3 and 6, such as for instance at 5. Alternatively, or in addition, a weight factor w(r) may be used. The weight factor w(r) may be computed based on the distance from the original seed point that is indicated by the user in the pulp chamber. First, a 3D distance map d(r) is computed with respect to this seed point. The weight factor w(r) may be defined as the sigmoid function of the 3D distance map:

$$w(r) = 1 - \frac{1}{1 + \exp\left(-\frac{d(r) - b}{a}\right)} \quad (24)$$

For example, the values a=2 mm and b=5 mm may be chosen. When using this weight factor w(r), the update function U(r), for the current iteration may be defined as the weighted sum of the darkness term G(r), and the object feature term F(r):

$$U(r) = w(r)G(r) + (1 - w(r))F(r) \quad (46)$$

After the update values U(r) have been computed using equation (46) in a given iteration, the segmentation mask may be updated (step 413) by including therein the region of connected voxels having a positive U(r) value (for example $U(r) > 10^{-4}$ is used to avoid noise effects) that comprises the seed voxel. The voxels having a positive U(r) value are a form of candidate image elements according to step 411. The region of connected voxels having a positive U(r) value that comprises the seed voxel is a form of region retained according to step 412.

G. Termination of the Segmentation

May for example be as explained in section 2.F.

A segmentation process according to an embodiment of the second exemplary set of embodiments may be further explained as follows:

Segmentation Process for Root Canal Detection in an Embodiment of the Second Exemplary Set of Embodiments.

```
1:  User selects a seed point in the pulp chamber (step 200).
2:  Initialize segmented mask S₀(r) based on the seed point (step 300).
3:  Compute C(r) and P(r) using equations (15)) and (16) (step 100).
4:  Compute gray level weight w(r) using equation (24).
5:  For k = 1, ..., k_max
6:      Include directionality function D(r) to compute Ĉ(r) and P̂(r) using equations
        (40) and (41) (step 411).
7:      Combine Ĉ(r) and P̂(r) into object feature filter O(r) using equation (42) and
        normalize (step 411).
8:      Compute c₁(r) and c₂(r) using equations (18) and (19) (step 411).
9:      Compute d₁(r) and d₂(r) using equations (44) and (45) (step 411).
10:     Compute darkness term G(r) using equation (23) (step 411).
11:     Compute object feature term F(r) using equation (43) (step 411).
12:     Compute update function U_k(r) using equation (26) (step 411).
13:     Update segmentation mask S_k(r) by including the region of connected voxels
        with positive U_k(r) that comprises the seed voxel (steps 411 to 413).
14:     if min_{l=1:k-1}(Σ|S_k(r) − S_l(r)|) ≤ v
15:         Stop.
16:     end
17: end
```

4. Third Exemplary Set of Embodiments: Segmentation of the Pulp Region

A. Preprocessing the Image Volume

May for example be as explained in section 2.A.

B. Initializing the Segmentation Mask

May for example be as explained in section 2.B.

C. Computing Curvature-Based Shape Recognition (CBSR) Terms (Also Referred to as Object Feature Detection Term)

May for example be as explained in section 2.C.

D. Gray Value Thresholding (GT)

May for example be as explained in section 2.D.

E. Identifying the Directionality of Recognized Shapes in Relation to that of the Segmentation Mask May for example be as explained in section 3.E.

F. Two-Phase Segmentation Process

In the third exemplary set of embodiments, the segmentation process comprises at least two phases, including a first phase and a second phase. The first phase may be as described above in sections 2 and 3, and comprises at least above-described steps 100, 200, 300, and 400, including update procedure 410 (see FIG. 1). At the end of the first phase, a segmentation mask is eventually outputted, which comprises a region of connected image elements comprising the seed. The second phase comprises at least above-described step 500, including enhanced update procedure 510 (see FIG. 2), or step 500, including enhanced update procedure with nested subprocedure (see FIG. 3). The second phase notably aims at incorporating, within the segmentation mask, potential portion(s) of the pulp region being separated by calcification from the region comprising the seed.

The second phase comprises an extended directionality procedure (see section 4.1 below), which is of limited use in the initial iterations when the segmentation mask only comprises (parts of) the pulp chamber. Since the extended directionality procedure is particularly useful in the root canal segments of the pulp region, it is desirable that this procedure be only used when at least parts of the root canals are comprised in the segmentation.

Therefore, during the first p iterations of the segmentation mask update (with p being for example a value comprised between 1 and 10, such as for example p=2, 3, 4, 5, 6 or 7), i.e. during the first phase, updating 413 the segmentation mask is limited to a region of connected image elements, with said region comprising the seed. After p iterations, it is expected that the segmentation mask has moved beyond the pulp chamber. The second phase may then start.

G. Combining Terms (First Phase) (Step 400)

May for example be as explained in section 2.E or section 3.F.

H. Combining Terms (Second Phase)

This process may be for example implemented as described in section 3.F, except that, in the second phase, after the update values U(r) have been computed using equation (46) in a given iteration, the regions of connected voxels having a positive U(r) value (for example U(r)>$10^{-4}$ is used to avoid noise effects) are retained in a temporary segmentation mask T(r) (including any region not comprising the seed). These regions of connected image elements (e.g., voxels) are also referred to as connected components (CC).

I. Extended Directionality: Retaining Regions of Connected Image Elements (e.g., Voxels) in the Assumed Root Canal Path (Second Phase)

Figure 10:
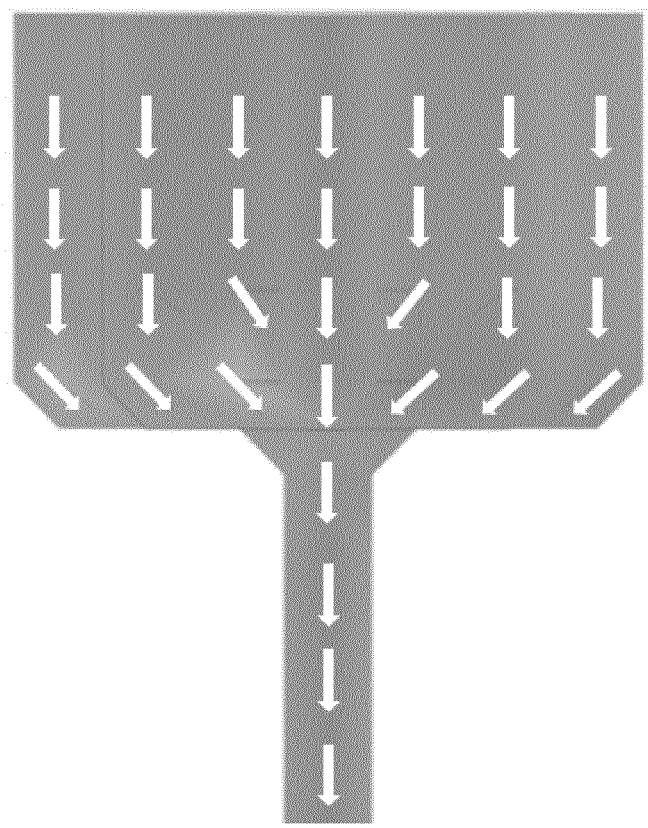
FIG. 10 shows, to assist in understanding some embodiments of the development, the discontinuity of characteristic eigenvectors at the location of a sudden jump in the width of a root canal.

The temporary segmentation mask T(r), which is obtained after every iteration, may not only contain segments of the pulp region, but may also comprise (parts of) other structures, such as structures surrounding the root canals, that may have a tubular or sheet-like character and low gray value. Furthermore, at the location of either a small calcification, a bifurcation, or a sudden change in cross-section, the directionality function D(r) (discussed in section 3.E) may be discontinuous because the characteristic eigenvectors are locally disrupted by one of these phenomena (see e.g. FIG. 10 showing a sudden change in cross-section). At these locations, which are typically present in the root canal segments of the pulp region, the segmentation may become disconnected.

To keep the regions of connected image elements representing the root canal, while excluding the other regions of connected image elements of the temporary segmentation mask T(r) from the final segmentation mask S(r), an intermediate segmentation mask M(r) may be initialized by including the region comprising the seed voxel (such region being referred to as the main connected component ($CC_m$)) (step 513, 613). Thereafter, the apex points of the intermediate segmentation mask M(r) may be determined.

The determination of the apex voxels $\{p_a\}$ within the intermediate segmentation mask M(r) may start with computing a distance function $D_g$ of all the voxels in the intermediate segmentation mask M(r) in relation to a start voxel $p_{start}$. Start voxel $p_{start}$ may be selected as a voxel assumed to be within the pulp chamber, such as within the center of the pulp chamber. Start voxel $p_{start}$ may for instance be the seed voxel or, alternatively, may be received from a user indicating a position that is within intermediate segmentation mask M(r) and is assumed to be within the pulp chamber. The distance measure may be geodesic, i.e. confined to the segmentation, and Euclidean. The geodesic Euclidean distance map may be computed iteratively by starting from an initial image M(r) with the same size as the binary mask image M of the pulp region and value 1000 at every voxel, except for the start voxel that has value 0. A list of "moving front" voxels surrounding the starting voxel are initialized in relation to the starting voxel (i.e. 1, $\sqrt{2}$ and $\sqrt{3}$ in the cardinal, ordinal and diagonal directions, respectively). For each of the foreground voxels in the 26-neighborhood of a moving front voxel, it is checked whether their current value is larger than the value at the current moving front voxel plus the (dimensionless) geodesic distance to the current moving front voxel (i.e. 1, $\sqrt{2}$ and $\sqrt{3}$ in the cardinal, ordinal and diagonal directions, respectively). If so, the value of distance function $D_g$ at that voxel is updated to the new lower value and the coordinates of the updated voxels are added to the moving front list (thereby removing the original voxel). The same update procedure is iteratively repeated for the 26-neighborhood of all the voxels in the list, until the list is empty and distance function $D_g$ has converged to the desired geodesic Euclidean distance map.

Figure 16:
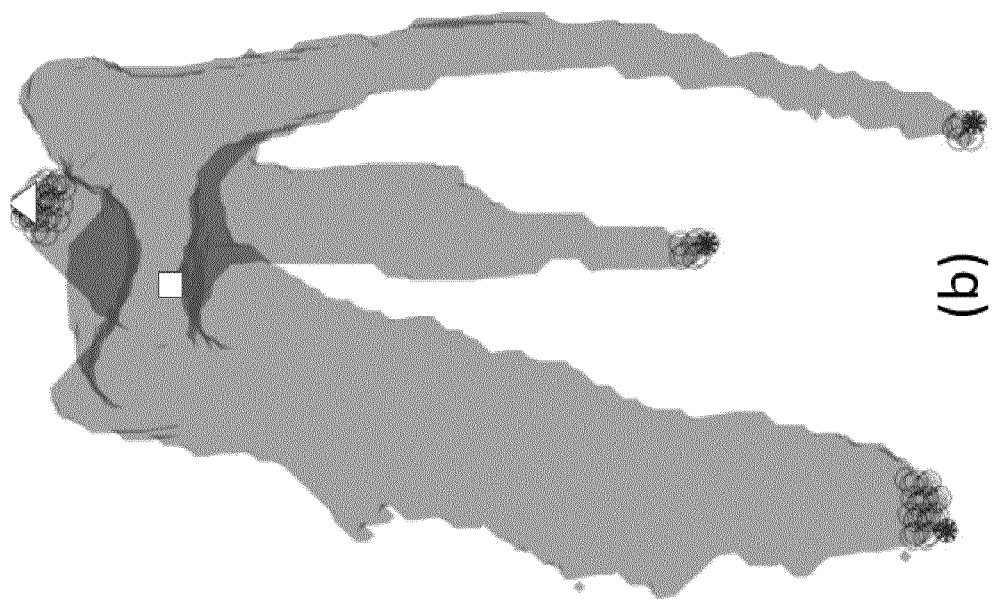
Figure 16:
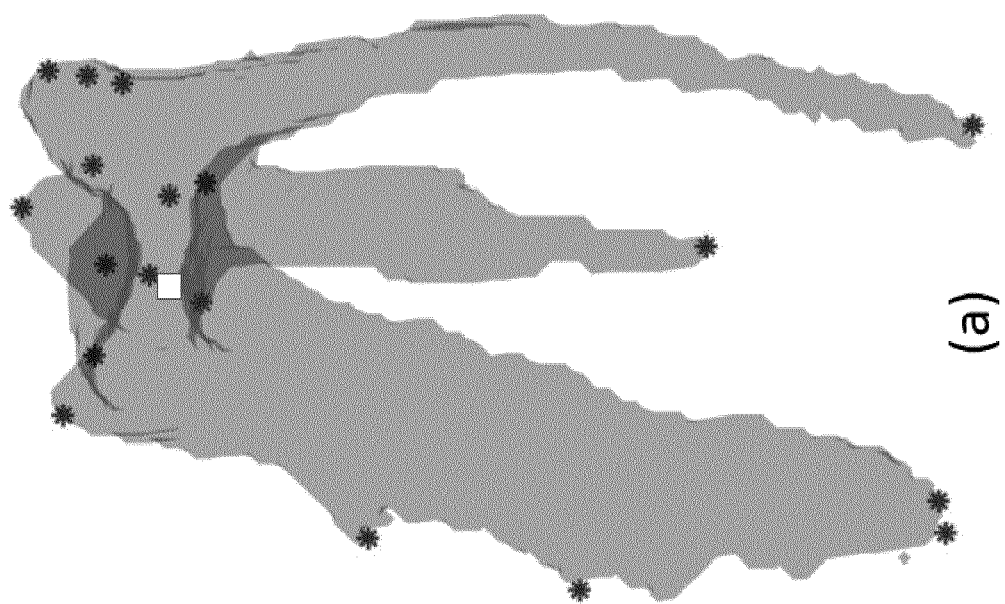

The resulting distance function $D_g$ has a) many local maxima, while b) the root apices are not all located at maximal global distance. The local maxima, illustrated in FIG. 16a, are first pruned by putting them and their neighboring voxels with values larger than $d_{max}$-c to value $d_{max}$-c, with $d_{max}$ being the local maximum value and parameter c being for example equal to 4 voxels. Then, the local maxima regions of this pruned image are identified. In each of these regions, the voxel with the maximal distance value in the original distance function $D_g$ (before pruning) is considered as an apex candidate. The pruning effectively removes the local maxima from the apex candidates, without making assumptions about the number of apices to be found. The pruning procedure is schematically illustrated on a toy image in FIG. 15. For illustrative reasons, the Manhattan distance and parameter c=3 are used, while an Euclidean distance and c=4 may alternatively be used. FIG. 15(a) shows the local maxima (stars) of the distance to start voxel $p_{start}$ (square). FIG. 15(b) shows the pruned distance functions (underlined values) with indication of local maximum region (circles) and local maximum of the original distance function $D_g$ in this region (star) indicating the final found apex candidate.

As illustrated in FIG. 16b, this may result in apex candidates that are located at extrema of the pulp chamber. To remove these false apex candidates, the apex candidate at an overall maximal distance from $p_{start}$ is identified and considered to certainly be an apex voxel. The straight line between this apex voxel and the start voxel can be used to evaluate the other candidate apices. To this end, all candidates for which the connection between them and the start voxel makes an angle of more than 70 degrees with said defined straight line are eliminated. This eliminates the candidate voxels in the pulp chamber, without making any directionality assumptions. After removing these pulp chamber candidate voxels, the remaining candidate apex voxels are retained as the apex points of intermediate segmentation mask M(r).

The apex candidate (white triangle in FIG. 16(b)) in the pulp chamber is removed based on the angle it makes with respect to the start voxel $p_{start}$ and the furthest apex candidate. The stars indicate the final apex voxels.

For every apex point, the connected components $CC_i$ of T(r) (i.e., the regions of connected image elements of T(r)) are identified for which the following conditions are satisfied: (i) the mean distance from the seed point is greater than the distance between an apex point and the seed point, and (ii) the connected component CC, (i.e., the region) is partially within a spherical region that contains said apex point and has a radius that is (for example) equal to twice the maximal σ value used for computing the tubular and sheet-like filter values (for example, the radius may be set at to 2×3=6 voxels). Each of these regions $CC_i$ is retained as a segmentation extension candidate and it is checked whether it is positioned in a direction relative to the apex point that is assumed to correspond with the path of the root canal. To this end, the part of intermediate segmentation mask M(r) that is contained within the above-described spherical region is defined as the nearby root canal region. The center of this region is connected with every voxel of region $CC_i$ as an indication of the direction of region $CC_i$. Subsequently, each of these directions is compared with the characteristic eigenvectors of the nearby root canal region. For voxels in said nearby canal region for which the characteristic eigenvector corresponds to the smallest eigenvalue (i.e. voxels with tubular character), the squared cosine of the angle between the direction vectors and the characteristic eigenvectors should be close to 1 for a region $CC_i$ to be in the direction of the nearby canal. For voxels in said nearby canal region for which the characteristic eigenvector corresponds to the largest eigenvalue (i.e. voxels with sheet-like character), the squared sine of this angle should be close to 1 for a region $CC_i$ to be in the direction of the nearby canal. A cut-off may be used in the sense that regions $CC_i$ are added to the intermediate segmentation mask M(r) only if the mean squared cosine or sine is larger than 0.8, corresponding to an average angle of 26.5 degrees.

After a region $CC_i$ is added to the intermediate segmentation mask M(r), the segmentation mask S(r) can be updated using M(r), and the segmentation procedure may continue with a following iteration (unless the termination criteria are met), wherein C(r), P(r), G(r) and F(r) are computed based on the updated segmentation mask S(r) (enhanced update procedure 510, see FIG. 2).

Alternatively, the addition of a region $CC_i$ to the intermediate segmentation mask M(r), a new apex point is determined for this updated intermediate segmentation mask, which is subsequently used in the evaluation of additional candidate regions. When no more regions can be identified for inclusion in the intermediate segmentation mask M(r), the segmentation mask S(r) is updated using M(r) and the segmentation procedure may continue with a following iteration (unless the termination criteria are met), wherein C(r), P(r), G(r) and F(r) are computed based on the updated segmentation mask S(r) (enhanced update procedure 610 with nested subprocedure, see FIG. 3).

J. Termination of the Segmentation

The termination may for example be as explained in section 2.F. In addition, it is desirable that, in the third exemplary set of embodiments, the termination criteria for convergence of the segmentation procedure are only evaluated after p+1 iterations (p is defined in section 4.F) or more, so that the extended directionality procedure (including enhanced update procedure 510, or enhanced update procedure with nested subprocedure 610) for catching possible "loose" regions relevant to the root canal segmentation is applied at least once.

K. Post-Processing: Connecting Segmented Pulp Region Parts

In one embodiment, after convergence of the segmentation process 500 or 600, the non-connected regions of the segmented root canal are joined together by a post-processing step that connects the 18-connected components that are not too far apart and removes the others, starting from the main region ($CC_m$) that comprises the seed voxel. A suitable procedure for merging the main region $CC_m$ and a neighboring region $CC_i$ may comprise separately dilating the binary mask of region $CC_m$ with a radius of for instance 6 and 5 voxels and subtracting both dilated images to retain a dilated "shell" of region $CC_m$. The intersection of this shell with the region $CC_i$ yields a region $s_i$. This may be repeated with region $CC_m$ and region $CC_i$ interchanged, to obtain the shell of region $CC_i$ and finally, region $s_m$. Then, every voxel of region $s_m$ may be connected with every voxel of region $s_i$, densely sampling along the connection lines, thus extending region $CC_m$ with region $CC_i$, including the connection. For regions $CC_i$ being too remote from others or being too small, region $s_i$ will be empty, resulting in no connection being made and the region $CC_i$ being removed from the final segmentation mask.

A segmentation process according to an embodiment of the third exemplary set of embodiments may be further explained as follows:

Segmentation Process for Root Canal Detection in an Embodiment of the Third Exemplary Set of Embodiments.

1: User selects a seed point in the pulp chamber (step 200).
2: Initialize segmented mask $S_0(r)$ based on the seed point (step 300).
3: Compute C(r) and P(r) using equations (15)) and (16) (step 100).
4: Compute gray level weight w(r) using equation (24).
5: For k = 1, ..., $k_{max}$
6:    Include directionality term D(r) to compute $\hat{C}(r)$ and $\hat{P}(r)$ using equations (40) and (41) (step 411).
7:    Combine $\hat{C}(r)$ and $\hat{P}(r)$ into object feature filter O(r) using equation (42) and normalize (step 411).
8:    Compute $c_1(r)$ and $c_2(r)$ using equations (18) and (19) (step 411).
9:    Compute $d_1(r)$ and $d_2(r)$ using equations (44) and (45) (step 411).
10:    Compute darkness term G(r) using equation (23) (step 411).
11:    Compute object feature term F(r) using equation (43) (step 411).
12:    Compute update function $U_k(r)$ using equation (26) and include all connected voxels with positive $U_k(r)$ values to the intermediate segmentation mask $T_k(r)$ (step 411).

-continued

```
13:    Update intermediate segmentation mask M_k(r) by including the region of
       connected voxels from T_k(r) that comprises the seed voxel (step 411 to 413).
14:    if k > n (for instance n = 5)
15:        Further update intermediate segmentation mask M_k(r) by adding (a)
           regions of connected voxels of the temporary segmentation mask T_k(r) that
           are estimated to be within the path of a root canal (step 500 or 600).
16:        Update segmentation mask S_k(r) using M_k(r) (step 515 or 618).
17:        if min_{l=1:k-1}(Σ|S_k(r) − S_l(r)|) ≤ v
18:            Stop.
19:        end
20:    end
21: end
22: Connect nearby segmented parts and remove distal parts.
```

5. Experimental Data

The segmentation method was tested on three data sets. The first data set, i.e. data set No. 1, comprised eight different teeth images that were cropped from special purpose endo CT images of two different patients. The second data set, i.e. data set No. 2, was obtained from sixteen extracted teeth that were conserved in either alcohol or an empty container for several years, then positioned in wax and scanned using a CBCT scanner. The third data set, i.e. data set No. 3, comprised five teeth images that were cropped from (no special purpose endo) CBCT images of different patients. All images had an isotropic 0.2 mm resolution or were resampled to this resolution during the pre-processing phase. The pulp regions in all images were segmented using the process according to an embodiment of the third exemplary set of embodiments (including enhanced update procedure with nested subprocedure 610) and the parameters as described previously. The seed point for all cases was selected manually in the middle of the pulp chamber. The segmentations performed using respectively featureness sensitivity factor $f_s=1$ and $f_s=2$ (after segmentation with $f_s=1$ the obtained segmentation result was used as initial segmentation mask for a segmentation procedure with $f_s=2$) were visually assessed, see Table 3. All images were properly segmented.

TABLE 3

Overview of the segmentation results of the three data sets.

| | Number of successful segmentations a) with $f_s = 1$, or b) with fs = 1 followed by $f_s = 2$ based on the result obtained with $f_s = 1$ | Number of successful segmentations with $f_s = 1$ only | Number of successful segmentations with $f_s = 2$ only |
|---|---|---|---|
| | Total number of teeth images | | | |
| Data set No. 1 | 8 | 8 | 7 | 7 |
| Data set No. 2 | 16 | 16 | 14 | 15 |
| Data set No. 3 | 5 | 5 | 4 | 4 |

Figure 11:
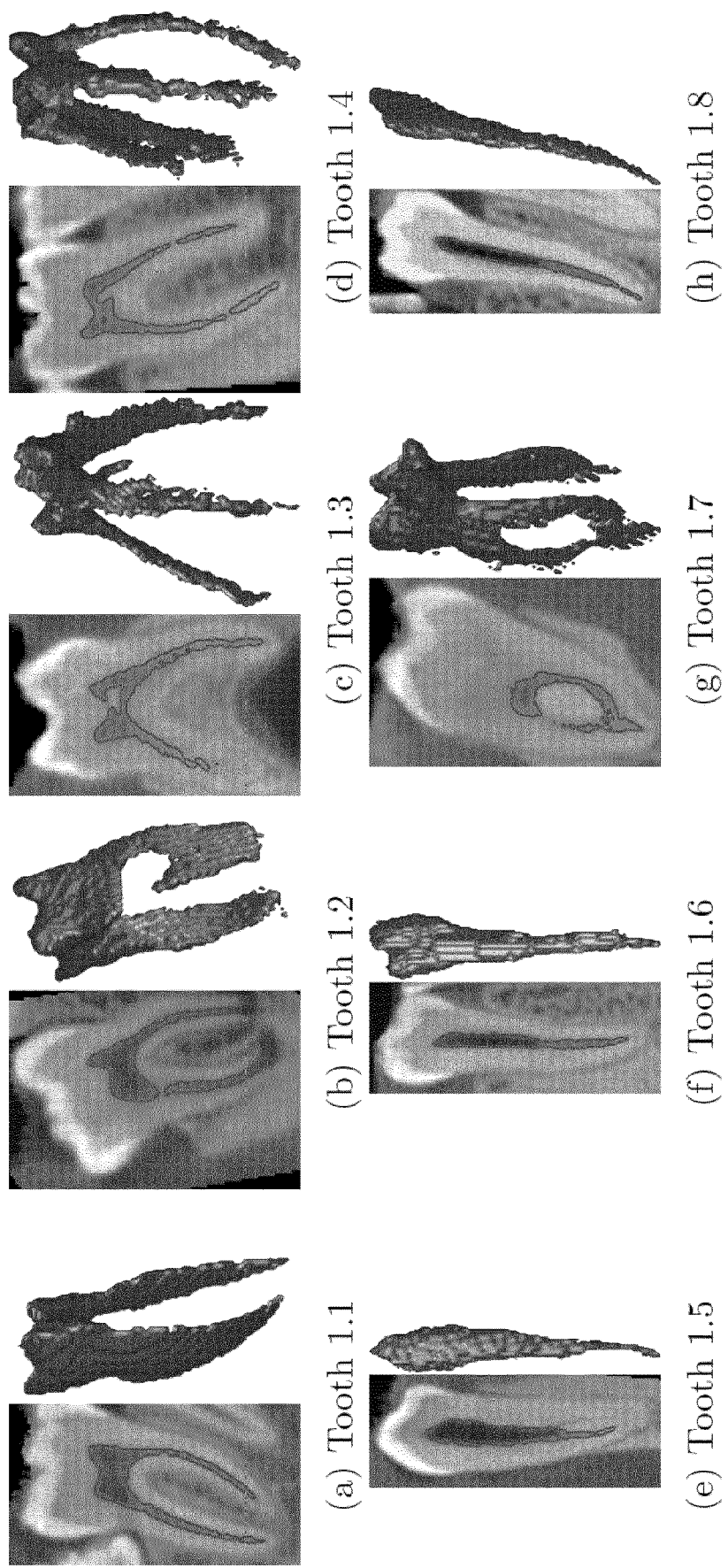
FIG. 11 shows, to assist in understanding some embodiments of the development, results of root canal segmentation of a data set No. 1 with special-purpose endo CT images.

FIG. 11 shows the segmentation results for data set No. 1 on 2D slices through the 3D volumes, for $f_s=1$. These results show that multiple canals, bifurcations, merging regions and obstructions are all dealt with appropriately. FIG. 11(*b*) shows a case where the tooth is open at the apical end of the root canal. Nevertheless, the segmentation nicely stops at the interior part of the tooth. This is explained by the directionality term D(r) of the object feature term O(r) detecting sudden direction changes, thus avoiding that the segmentation grows outside the root canal itself.

It was observed that, although a value of $f_s=1$ gives satisfactory results for most cases, in some cases the segmentation result is slightly improved by increasing the value of featureness sensitivity factor $f_s$ to 2 and iterating the segmentation procedure starting from the result obtained using $f_s=1$. FIG. 12(*a*) shows the result for tooth 1.5 (the "failed" case for $f_s=1$ in Table 3), for which a small bifurcation near the apex was missed with $f_s=1$ (FIG. 11(*e*)), but was properly captured with $f_s=2$. On the other hand, for tooth 1.2, which was satisfactorily segmented with $f_s=1$ (FIG. 11(*b*)), the use of $f_s=2$ (FIG. 12(*b*)) resulted in clear oversegmentation (the "failed" case for $f_s=2$ in Table 3). For the other six cases, there was no clear difference between segmentation results obtained with $f_s=1$ or $f_s=2$.

FIG. 13 shows two results from data set No. 2. The high curvature of the root canal near the apex of tooth 2.1 is nicely captured in FIG. 13(*a*). FIGS. 13(*b*) and (*c*) show the segmentation of a tooth with two bifurcating root canals that merge at the apical side of the tooth. When using $f_s=1$ a discontinuity remains near the merging location of the canals (a "failed" case for $f_s=1$ in Table 3; FIG. 13(*b*)), this discontinuity is closed when increasing featureness sensitivity factor $f_s$ to 2 (FIG. 13(*c*)).

FIG. 14 shows two results from data set No. 3. These CBCT images, which were not specifically acquired for endodontic purposes, are noisier, and the root canals are visually less clear than in the images of datasets 1 and 2. The noise increases the risk of segmentation outside of the pulp region. In view of this risk, the result of FIG. 14(*a*) was obtained using first $f_s=0.5$ to obtain a careful, limited segmentation, which was then used for a further segmentation with $f_s=1$ (after segmentation with $f_s=0.5$ the obtained segmentation result is used as initial segmentation mask for a segmentation procedure with $f_s=1$). For the result shown in FIG. 14(*b*), the featureness sensitivity factor $f_s$ was increased from 1 to 2 to close all the gaps at the location where root canals merge.

6. Further Embodiments and Considerations

Figure 17:
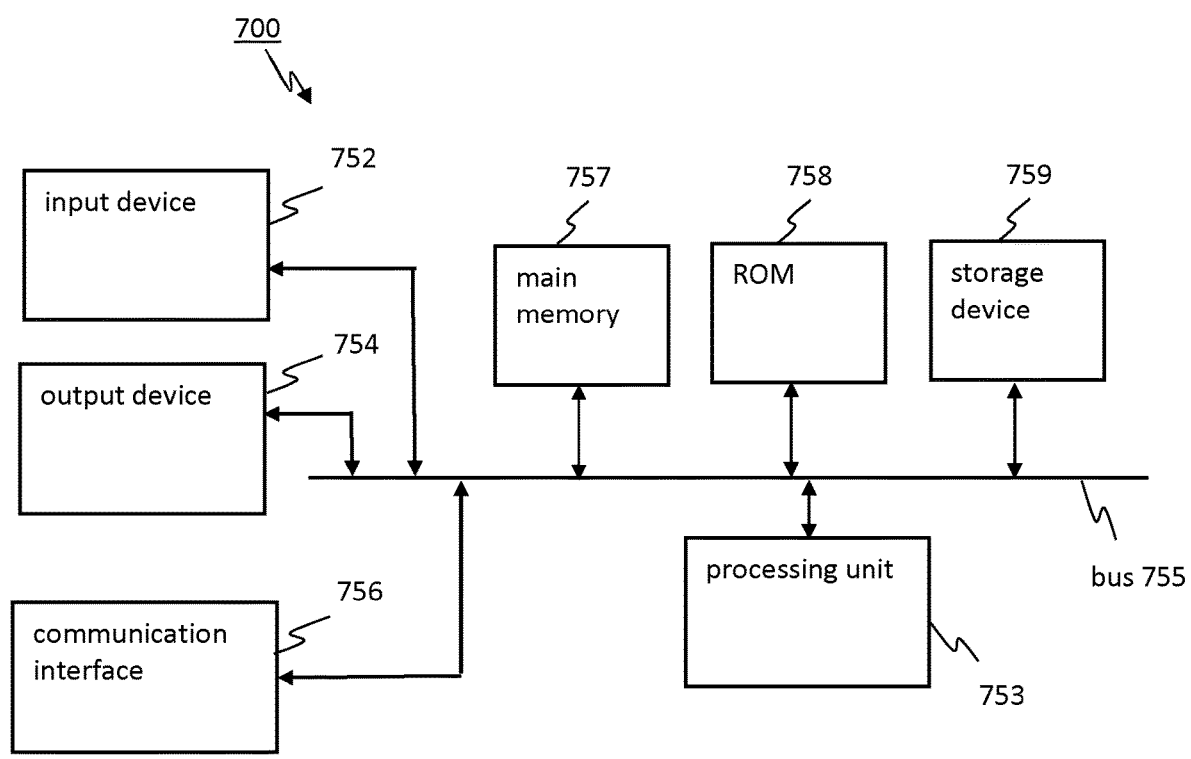
FIG. 17 is a schematic diagram of an exemplary implementation of a system according to one embodiment of the development.

FIG. 17 is a schematic diagram of an exemplary implementation of a system 700 that may be used in embodiments of the development.

As illustrated by FIG. 17, system 700 may include a bus 755, a processing unit 753, a main memory 757, a ROM 758, a storage device 759, an input device 752, an output device 754, and a communication interface 756. Bus 755 may include a path that permits communication among the components of system 700.

Processing unit 753 may include a processor, a microprocessor, or processing logic that may interpret and execute instructions. Main memory 757 may include a RAM or another type of dynamic storage device that may store information and instructions for execution by processing unit 753. ROM 758 may include a ROM device or another type of static storage device that may store static information and instructions for use by processing unit 753. Storage device 759 may include a magnetic and/or optical recording medium and its corresponding drive.

Input device 752 may include a mechanism that permits a user to input information to system 700, such as a keypad, a keyboard, a mouse, a pen, voice recognition and/or biometric mechanisms, etc. Output device 754 may include a mechanism that outputs information to the user, including a display, a printer, a speaker, etc. Communication interface 756 may include any transceiver-like mechanism, or receiver and transmitter, that enables system 700 to communicate with other devices and/or systems (such as with an imaging apparatus as mentioned above, etc.). For example, communication interface 756 may include mechanisms for communicating with another device or system via a telecommunication network.

System 700 may perform certain operations or processes described herein. These operations may be performed in response to processing unit 753 executing software instructions contained in a computer-readable medium, such as main memory 757, ROM 758, and/or storage device 759. A computer-readable medium may be defined as a physical or a logical memory device. For example, a logical memory device may include memory space within a single physical memory device or distributed across multiple physical memory devices. Each of main memory 757, ROM 758 and storage device 759 may include computer-readable media. The magnetic and/or optical recording media (e.g., readable CDs or DVDs) of storage device 759 may also include computer-readable media. The software instructions may be read into main memory 757 from another computer-readable medium, such as storage device 759, or from another device via communication interface 756.

The software instructions contained in main memory 759 may cause processing unit 753 to perform operations or processes described herein, such as above-described steps 100, 200, 300, and 400. Alternatively, hardwired circuitry may be used in place of or in combination with software instructions to implement processes and/or operations described herein. Thus, implementations described herein are not limited to any specific combination of hardware and software.

Where the terms "curvature-based shaped recognition unit", "seed indication receiving unit", "using unit", and "update unit", etc. are used throughout the above description, no restriction is made regarding how distributed these elements may be and regarding how gathered elements may be. That is, the constituent elements of a unit, function or network node may be distributed in different software or hardware components or devices for bringing about the intended function. A plurality of distinct elements may also be gathered for providing the intended functionalities. In particular, in a server-client architecture or the like, a part of the segmentation process may be carried out on a server computer (or in the cloud in the sense of cloud computing) located away from, and communicably connected to, a client computer being in charge of the input and output interactions with the end user, and another part of the segmentation process may be carried out on the client computer.

Any one of the above-referred units may be implemented in hardware, software, field-programmable gate array (FPGA), application-specific integrated circuit (ASICs), firmware or the like.

In further embodiments of the development, any one of the above-mentioned curvature-based shaped recognition unit, seed indication receiving unit, using unit, update unit, etc. is replaced by curvature-based shaped recognition means, seed indication receiving means, using means, update means, etc. or curvature-based shaped recognition module, seed indication receiving module, using module, update module, etc. respectively, for performing the functions of the curvature-based shaped recognition unit, seed indication receiving unit, using unit, update unit, etc.

In further embodiments of the development, any one of the above-described procedures, steps or processes may be implemented using computer-executable instructions, for example in the form of computer-executable procedures, methods or the like, in any kind of computer languages, and/or in the form of embedded software on firmware, integrated circuits or the like.

Although the present invention has been described on the basis of detailed examples, the detailed examples only serve to provide the skilled person with a better understanding, and are not intended to limit the scope of the invention. The scope of the invention is much rather defined by the appended claims.

ABBREVIATIONS 2D two-dimensional
3D three-dimensional
ASICs application-specific integrated circuit
CBCT cone beam computed tomography
CBSR curvature-based shape recognition
CC connected components
CT computed tomography
DICOM Digital Imaging and Communications in Medicine
FPGA field-programmable gate arrays
GT grayscale thresholding (also called: gray value thresholding)
GUI graphical user interface
PCA principal component analysis
PVE partial volume effects
RAM random-access memory
ROI region of interest
ROM read-only memory

REFERENCES

[1] C. Lost. Quality guidelines for endodontic treatment: consensus report of the European Society of Endodontology. *International Endodontic Journal*, 39:921-930, 2006.
[2] Dentsply Sirona. 3D Endo™ Software. https://www.3dendo.com/. Accessed: May 29, 2017.
[3] A. F. Frangi, W. J. Niessen, L. Vincken, and M. A. Viergever. Multiscale vessel enhancement filtering. *Lecture Notes in Computer Science*, 1496:130-137, 1998.
[4] M. Descoteaux, M. Audette, K. Chinzei, and K. Siddiqi. Bone enhancement filtering: Application to sinus bone segmentation and simulation of pituitary surgery. *Computer aided surgery*, 11(5):247-255, 2010.
[5] S. Lankton and A. Tannenbaum. Localizing region-based active contours. *IEEE Transactions on Image Processing*, 17(11):2029-2039, 2008.

[6] F. Peracchi. Robust m-estimators of regression. *Giornale degli Economisti e Annali di Economia*, 46(9):533-545, 1987.

[7] C. Jud and T. Vetter. Using object probabilities in deformable model fitting. 2014 *22nd International Conference on Pattern Recognition.* 3310-3314, 2014

The invention claimed is:

1. A computer-implemented method for segmenting a tooth's pulp region from a 2D or 3D image of the tooth, wherein the pulp region comprises a pulp chamber and one or more root canals, the method comprising:
    performing a curvature-based shape recognition at different spatial scales using smoothed versions of the image;
    receiving an indication of a point or region assumed to be located in the imaged pulp chamber of the image and corresponding to at least one image element of the image, the at least one image element being hereinafter referred to as "seed";
    using at least the seed as initial segmentation mask; and
    iteratively carrying out an update procedure, comprising:
        determining candidate image elements for updating the segmentation mask, wherein determining comprises:
            in at least the first n iteration(s) of the update procedure, a grayscale thresholding taking as reference the current segmentation mask, wherein n is a nonzero positive integer; and,
            in at least one iteration of the update procedure, taking the curvature-based shape recognition into account;
        retaining, among the candidate image elements, a region of connected candidate image elements, the region comprising the seed; and
        using the retained region to update the segmentation mask;
    wherein the grayscale thresholding taking as reference the current segmentation mask comprises determining the differences between the intensity level of an image element under consideration and an averaged foreground and background intensity value, respectively, wherein the averaged foreground value is computed as the average intensity value of image elements comprised in the current segmentation mask and wherein the averaged background intensity value is computed as the average intensity value of image elements outside the current segmentation mask.

2. The method according to claim 1, wherein the averaged foreground and/or background intensity values are computed for the image elements within an image region centered around the image element under consideration.

3. The method of claim 1, wherein computing the averaged foreground and/or background value intensity values comprises calculating a weighted average, wherein the weight of the intensity value of an image element decreases with increasing distance between the image element and the image element under consideration.

4. The method of claim 3, wherein calculating the weighed average comprises using a weighing mask centered around the image element under consideration.

5. The method according to claim 1, wherein, in at least one iteration of the update procedure, the grayscale thresholding and the curvature-based shape recognition are both performed.

6. The method of claim 5, wherein, in at least one iteration in which the grayscale thresholding and the curvature-based shape recognition are both performed, an importance or weight associated, for an image element under consideration, to the curvature-based shape recognition relative to the grayscale thresholding increases with increasing distance of the image element from the seed.

7. The method according to claim 1, wherein, in at least one iteration in which the curvature-based shape recognition is performed, determining candidate image elements further takes into account a directionality of a recognized shape at the level of an image element in comparison to an overall directionality of a portion of the segmentation mask near the image element.

8. The method according to claim 1, further comprising, after having iteratively carried out the update procedure:
    iteratively carrying out an enhanced update procedure, comprising:
        determining candidate image elements for updating the segmentation mask, wherein determining comprises taking into account the curvature-based shape recognition and a directionality of a recognized shape at the level of an image element in comparison to an overall directionality of a portion of the segmentation mask near the image element;
        retaining, among the candidate image elements, a first region of connected candidate image elements, wherein the first region comprises the seed;
        using the retained first region to form an intermediate segmentation mask;
        retaining, among the candidate image elements, a second region of connected candidate image elements, wherein the second region is not connected to the intermediate segmentation mask and is positioned apically from the intermediate segmentation mask in a direction consistent with a directionality of an apical portion of the intermediate segmentation mask nearest to the second region; and
        using the intermediate segmentation mask and the retained second region to update the segmentation mask.

9. The method according to claim 1, further comprising, after having iteratively carried out the update procedure:
    iteratively carrying out an enhanced update procedure with nested subprocedure, comprising:
        determining candidate image elements for updating the segmentation mask, wherein determining comprises taking into account the curvature-based shape recognition and a directionality of a recognized shape at the level of an image element in comparison to an overall directionality of a portion of the segmentation mask near the image element;
        retaining, among the candidate image elements, a first region of connected candidate image elements, wherein the first region comprises the seed;
        using the retained first region to form an intermediate segmentation mask;
        iteratively carrying out a nested subprocedure, comprising:
            retaining, among the candidate image elements, a further region of connected candidate image elements, wherein the further region is not connected to the intermediate segmentation mask and is positioned apically from the intermediate segmentation mask in a direction consistent with a directionality of an apical portion of the intermediate segmentation mask nearest to the further region; and
            adding the further region to the intermediate segmentation mask;

using the intermediate segmentation mask to update the segmentation mask.

10. The method according to claim 8, wherein determining candidate image elements for updating the segmentation mask further comprises grayscale thresholding taking as reference the current segmentation mask.

11. The method according to claim 10, wherein, in at least one iteration of the enhanced update procedure or of the enhanced update procedure with nested subprocedure, whichever enhanced update procedure is applicable, an importance or weight associated, for an image element under consideration, to the curvature-based shape recognition relative to the grayscale thresholding increases with increasing distance of the image element from the seed.

12. The method according to claim 1, wherein in an iteration of the update procedure an image element included in the segmentation mask from the previous iteration may be discarded from the updated segmentation mask.

13. The method according to claim 1, wherein the segmentation mask grows from one iteration to the next.

14. The method according to claim 1, wherein, in an iteration, image elements at a distance larger than a threshold distance from the current segmentation mask are disregarded.

15. The method according to claim 1, wherein iterating is stopped when the new segmentation mask differs from the current segmentation mask by fewer than m image elements, wherein m is a nonzero positive integer.

16. The method according to claim 1, wherein the image is an X-ray image.

17. The method according to claim 1, wherein the curvature-based shape recognition comprises identifying shape structures corresponding to possible shapes of a root canal or segment thereof.

18. The method of claim 17, wherein the curvature-based shape recognition comprises at least one of: identifying tubular structures and identifying sheet-like structures.

19. The method according to claim 1, further comprising visually rendering an anatomy of the segmented tooth's pulp region.

20. The method according to claim 1, further comprising determining parameters of an anatomy of the segmented tooth's pulp region.

21. The method of claim 20, wherein determining parameters of an anatomy of the segmented tooth's pulp region comprises determining at least one of:
  widths along at least one root canal of the segmented tooth's pulp region;
  a center line of at least one root canal of the segmented tooth's pulp region; and
  a length of at least one root canal of the segmented tooth's pulp region.

22. The method according to claim 1, wherein the updated segmentation mask is used in a computer-based virtual planning of an endodontic procedure.

23. A system for segmenting a tooth's pulp region from a 2D or 3D image of the tooth, wherein the pulp region comprises a pulp chamber and one or more root canals, the system comprising a processing unit configured to:
  perform a curvature-based shape recognition at different spatial scales using smoothed versions of the image;
  receive an indication of a point or region assumed to be located in the imaged pulp chamber of the image and corresponding to at least one image element of the image, the at least one image element being hereinafter referred to as "seed";
  use at least the seed as initial segmentation mask; and
  iteratively carry out an update procedure, comprising:
    determining candidate image elements for updating the segmentation mask, wherein determining comprises:
    in at least the first n iteration(s) of the update procedure, a grayscale thresholding taking as reference the current segmentation mask, wherein n is a nonzero positive integer; and,
    in at least one iteration of the update procedure, taking the curvature-based shape recognition into account;
    retaining, among the candidate image elements, a region of connected candidate image elements, the region comprising the seed; and
    using the retained region to update the segmentation mask;
  wherein the grayscale thresholding taking as reference the current segmentation mask comprises determining the differences between the intensity level of an image element under consideration and an averaged foreground and background intensity value, respectively, wherein the averaged foreground value is computed as the average intensity value of image elements comprised in the current segmentation mask and wherein the averaged background intensity value is computed as the average intensity value of image elements outside the current segmentation mask.

24. A non-transitory computer readable medium comprising a computer program stored thereon comprising computer-readable instructions configured for, when executed on a computer, causing the computer to carry out the method according to claim 1.

25. The method according to claim 9, wherein determining candidate image elements for updating the segmentation mask further comprises grayscale thresholding taking as reference the current segmentation mask.

26. The method according to claim 25, wherein, in at least one iteration of the enhanced update procedure or of the enhanced update procedure with nested subprocedure, whichever enhanced update procedure is applicable, an importance or weight associated, for an image element under consideration, to the curvature-based shape recognition relative to the grayscale thresholding increases with increasing distance of the image element from the seed.

* * * * *